(12) United States Patent
Philpott et al.

US007943297B2

(10) Patent No.: US 7,943,297 B2
(45) Date of Patent: *May 17, 2011

(54) ANALYSIS OF HIV-1 CORECEPTOR USE IN THE CLINICAL CARE OF HIV-1-INFECTED PATIENTS

(75) Inventors: Sean Philpott, Albany, NY (US); Barbara Weiser, Albany, NY (US); Harold Burger, Albany, NY (US); Christina Kitchen, Los Angeles, CA (US)

(73) Assignee: Health Research Inc., Menands, NY (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/872,842

(22) Filed: Oct. 16, 2007

(65) Prior Publication Data

US 2008/0096209 A1   Apr. 24, 2008
US 2009/0117548 A2   May 7, 2009

Related U.S. Application Data

(62) Division of application No. 10/695,846, filed on Oct. 29, 2003, now Pat. No. 7,294,458, which is a division of application No. 09/963,064, filed on Sep. 25, 2001, now Pat. No. 6,727,060.

(60) Provisional application No. 60/235,671, filed on Sep. 26, 2000, provisional application No. 60/282,354, filed on Apr. 6, 2001.

(51) Int. Cl.
*C12Q 1/70* (2006.01)
*G01N 33/53* (2006.01)
*C12P 1/00* (2006.01)
*C12N 5/00* (2006.01)
*C12N 5/08* (2006.01)

(52) U.S. Cl. ............ 435/5; 435/7.1; 435/7.2; 435/7.24; 435/41; 435/325

(58) Field of Classification Search ........................ None
See application file for complete search history.

(56) References Cited

U.S. PATENT DOCUMENTS

| | | | |
|---|---|---|---|
| 5,837,464 A | 11/1998 | Capon et al. |
| 5,851,759 A | 12/1998 | Weiner |
| 5,994,515 A | 11/1999 | Hoxie |
| 6,107,019 A | 8/2000 | Allaway et al. |
| 7,097,970 B2 | 8/2006 | Petropoulos et al. |
| 7,169,551 B2 | 1/2007 | Petropoulos et al. |
| 2003/0180717 A1 | 9/2003 | Esteban et al. |
| 2005/0214743 A1 | 9/2005 | Richman et al. |
| 2006/0183110 A1 | 8/2006 | Petropoulos et al. |
| 2006/0223107 A1 | 10/2006 | Chenna et al. |
| 2009/0047662 A1 | 2/2009 | Philpott et al. |

FOREIGN PATENT DOCUMENTS

| | | |
|---|---|---|
| WO | WO 99 14378 A | 3/1999 |
| WO | 99/67429 | 12/1999 |
| WO | WO 00/65356 | 11/2000 |
| WO | WO 03/083094 | 10/2003 |

OTHER PUBLICATIONS

Martinez et al. Human Immunodeficiency Virus Type 1 Genetic Evolution in Patients with Prolonged Suppression of Plasma Viremia. Virology 1999, vol. 256, pp. 180-187.*
Yershov et al. DNA analysis and diagnostics on oligonucleotide microchips. The Proceedings from National Academy of Science, United States of America, May 1996, vol. 93, pp. 4913-4918.*
Hung et al. Analysis of the Critical Domain in the V3 Loop of Human Immunodeficiency Virus Type 1 gp120 Involved in CCR5 Utilization. Journal of Virology, Oct. 1999, vol. 73, No. 10, p. 8216-8226.*
Nelson, et al., "Evolutionary Variants of the Human Immunodeficiency Virus Type 1 V3 Region Characterized by Using a Heteroduplex Tracking Assay", Journal of Virology, Nov. 1997, vol. 71, No. 11, pp. 8750-8758.
L. Q. Zhang, et al., "Selection of Specific Sequences in the External Envelope Protein of Human Immunodeficiency Virus Type 1 upon Primary Infection", Journal of Virology, Jun. 1993, vol. 67, No. 6 pp. 3345-3356.
Shang Cao, et al., "Study on transient infection of T cell lines by M tropic HIV-1 strains", Chinese Journal of Experimental and Clinical Virology, vol. 13, No. 2, Jun. 1999, pp. 163-169.
Shan Li, et al., "Persistent CCR5 Utilization and Enhanced Macrophage Tropism by Primary Blood Human Immunodeficiency Virus Type 1 Isolates from Advanced Stages of Disease and Comparison to Tissue-Derived Isolates", Journal of Virology, Dec. 1999, vol. 73, No. 12, pates 9741-9755. Julie A. E. Nelson, et al., "Patterns of Changes in Human Immunodeficiency Virus Type 1 V3 Sequence Populations Late in Infection", Journal of Virology, Sep. 2000, vol. 74, No. 18, pp. 8494-8501.
Timothy J. Wilkin, et al., "HIV Type 1 Chemokine Coreceptor Use among Antiretroviral-Experienced Patients Screened for a Clinical Trial of a CCR5 Inhibitor: AIDS Clinical Trial Group A5211", Clinical Infectious Diseases, Feb. 15, 2007, vol. 44, No. 4, pp. 591-595.
Charlotte Tscherning-Casper, et al., "Coreceptor Usage of HIV-1 Isolates Representing Different Genetic Subtypes Obtained From Pregnant Cameroonian Women", Journal of Acquired Immune Deficiency Syndromes, vol. 24, No. 1, May 1, 2000, pp. 1-9.
Dalma Vodros et al., "Quantitative Evaluation of HIV-1 Coreceptor Usin in the GHOST (3) Cell Assay", Virology, vol. 291, No. 1, Dec. 5, 2001, pp. 1-11.

(Continued)

*Primary Examiner* — A R Salimi
*Assistant Examiner* — Louise Humphrey
(74) *Attorney, Agent, or Firm* — Vedder Price P.C.; Thomas J. Kowalski; Deborah L. Lu

(57) ABSTRACT

A change in viral tropism occurs in many HIV positive individuals over time and can be indicated by a change in coreceptor usage from CCR5 to CXCR4. The change in coreceptor usage to CXCR4 has been shown to correlate with increased disease progression. In patients undergoing HAART, the predominant populations of virus can be shifted back to CCR5-mediated entry after the CXCR4-specific strains have emerged. The present invention relates to a diagnostic method to monitor coreceptor use in the treatment of human immunodeficiency virus (HIV) infection. The present invention further relates to a diagnostic method applied to HIV-positive individuals undergoing HAART to monitor the suppression of CXCR4 specific strains. The diagnostic methods can be used to assist in selecting antiretroviral therapy and to improve predictions of disease prognosis over time.

7 Claims, 3 Drawing Sheets

OTHER PUBLICATIONS

Figure 1:
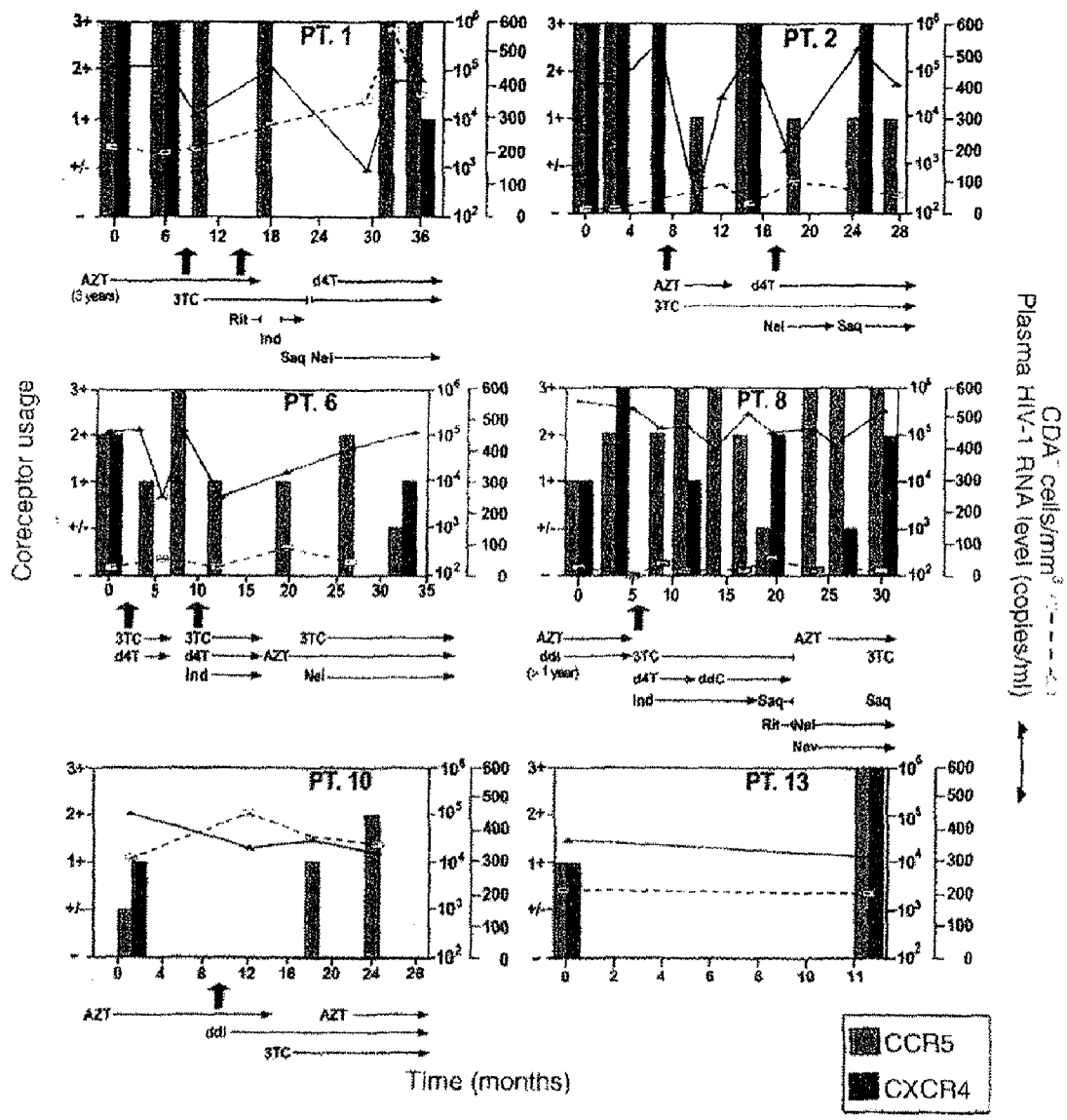

Paul R. Gorry et al., "Macrophage Tropism of Human Immunodeficiency Virus Type 1 Isolates from Brain and Lymphoid Tissues Predicts Neurotropism Independent of Coreceptor Specificity", Journal of Virology, Nov. 2001, vol. 75, No. 21, pp. 10073-10089.

Philpott S. et al. "Preferential suppression of CXCR4-specific strains of HIV-1 by antiviral therapy." J. Clin. Invest., vol. 107(4), Feb. 2001, p. 431-438.

Moore JP, et al. "Co-receptors for HIV-1 entry." Cur. Opin. Immunol., vol. 9, 1997, pp. 551-562.

Callaway DS, et al. "Virus phenotype switching and disease progression in HIV-1 infection." Proc. R. Soc. Lond., vol. 266, 1999 pp. 2523-2530.

Wodarz D, et al. "Defining CTL-induced pathology: implications for HIV." Virology, vol. 274, Aug. 2000, pp. 94-104.

Clerici, et al. (2000) "Different immunologic profiles characterize HIV infection in highly active antiretroviral therapy-treated and antiretroviral-naïve patients with undetectable viraemia. The Master Group". AIDS 14(2): 109-116.

Conner, et al. "Change in coreceptor use correlates with disease progression in HIV-1 infected individuals" J. Exp. Med. vol. 185(4). Feb. 17, 1997, pp. 621-628.

Bjomdal, et al. "Coreceptor usage of primary human immunodeficiency virus type 1 isolates varies according to biological phenotype" Journal of Virology, Oct. 1997, pp. 7478-7487.

Burger and Weiser, (1997) "Biology of HIV-1 in women and men" Obstetrics and Gynecology Clinics of North America, vol. 24, No. 4, pp. 731-742.

Pierson, et al. (2000) "Characterization of chemokine receptor utilization of viruses in the latent reservoir for human immunodeficiency virus type 1". J. Virol. 74(17): 7824-33.

Mosier (2000) "Virus and target cell evolution in human immunodeficiency virus type 1 infection", Immunologic Research, vol. 21, No. 2-3, pp. 253-258.

Verrier, et al. (1999) "Role of the HIV type 1 glycoprotein 120 V3 loop in determining coreceptor usage" AIDS Research and Human Retroviruses, vol. 15, No. 9, 1999, pp. 731-743.

Chan, et al. (1999) "V3 recombinants indicate a central role for CCR5 as a coreceptor in tissue infection by human immunodeficiency virus type 1" Journal of Virology, Mar. 1999, pp. 2350-2358.

Anderson, et al. (1998) "Early reduction of immune activation in lymphoid tissue following highly active HIV therapy" AIDS 12:F123-9.

Berger, et al. (1999) "Chemokine receptors as HIV-1-coreceptors: roles in viral entry, tropism and disease." Arum. Rev. Immunol 17:657-700.

Berkowitz, et al. (2000) "Casual relationships between HIV-1 coreceptor utilization, tropism, and pathogenesis in human thymus." J. AIDS Hum. Retro. 16(11):1039-45.

Cammack N. (1999) "Human Immunodeficiency virus type 1 entry and chemokine receptors: a new therapeutic target." Antivir. Chem. Chemother. 10(2):53-62.

Cecilia, et al. (2000) "Absence of coreceptor switch with disease progression in human immunodeficiency virus infections in India" Virology 271(2):253-8.

Dreyer, et al. (1999) "Primary isolate neutralization by HIV type 1-infected patient sera in the era of highly active antiretroviral therapy." AIDS Res. Hum. Retrovir 15(17):1563-1571.

Equils, et al. (2000) "Recovery of replication-competent virus from CD4 T cell reservoirs and change in coreceptor use in human immunodeficiency virus type 1-infected children responding to highly active antiretroviral therapy." J. Inf. Dis. 182:751-757.

Este, et al. (1999) "Shift of clinical human immunodeficiency virus type 1 isolates from X4 to R5 and prevention of emergence of the syncytium-inducing phenotype by blockade of CXCR4". J. Virol. 73:5577-85.

Fang, et al. (1996) "Molecular cloning of full-length HIV-1 genomes directly from plasma viral RNA". J. Acquir. Immune Defic. Syndr. Hum. Retrovirol. 12(4):352-7.

Giovannetti, et al. (1999) "CCR5 and CXCR4 chemokine receptor expression and beta-chemokine production during early T cell repopulation induced by highly active anti-retroviral therapy". Clin. Exp. Immunol. 118(1):87-94.

Glushakova, et al. (2000) "Preferential coreceptor utilization and cytopathicity by dual-topic HIV-1 in human lymphoid tissue ex vivo". J. Clin. Invest. 104:R7-R11.

Hotkamp, et al. (2000) "Unexpected coreceptor usage of primary human immunodeficiency virus type 1 isolates from viremic patients under highly active antiretroviral therapy." J. Inf. Dis. 181(2):513-21.

Kokkotou, et al. (2000) "In vitro correlates of HIV-2-mediated HIV-1 protection."Proc. Natl. Acad. Sci. USA 97(12):6797-8002.

Kusunoki, et al. (1999) "Antisense oligodeoxynulceotide complementary to CXCR4 mRNA block replication of HIV-1 in COS cells. "Nucleosides Nucleotides 18(6-7): 1705-8.

Lee, et al. (1999) "Quantification of CD4, CCR5, and CXCR4 levels on lymphocyte subsets, dendritic cells, and differentially conditioned monocyte-derived macrophages" Proc. Natl. Acad. Sci. USA 96(9):5215-20.

Lew, et al. (1998) "Determinations of levels of human immunodeficiency virus type 1 RNA in plasma: reassessment of parameters affecting assay outcome. TUBE Meeting Workshop Attendees. Technology Utilization for HIV-1 Blood Evaluation and Standardization in Pediatrics." J. Clin. Microbiology (36)6:1471-9.

Martinon, et al. (1999) "Persistent alterations in T-cell repertoire, cytokine and chemokine receptor gene expression after 1 year of highly active antiretroviral therapy." AIDS. 13(2):185-94.

Michael, et al. (1999) "Viral phenotype and CCR5 genotype", Nat. Med. 5(12):1330.

Philpott, et al. (1999) "Antiviral therapy may preferentially eliminate CXCR4-specific strains of HIV-1" Interscience Conference on Antimicrobial Agents and Chemotherapy (ICAAC) Moscone Center San Francisco, CA, USA, Sep. 26-29, 1999 Abstract 1836 p. 513.

Samson, et al. (1996) "Resistance to HIV-1 infection in Caucasian individuals bearing mutant alleles of the CCR-5 chemokine receptor gene", Nature 382:722-5.

Schramm, et al. (2000) "Viral entry through CXCR4 is a pathogenic factor and therapeutic target in human immunodeficiency virus type 1 disease", J. Virol. 74(1):184-92.

Shankarappa, et al. (1999) "Consistent viral evolutionary changes associated with the progression of human immunodeficiency virus type 1 infection", J. Virol. 73(12):10489-502.

Trkola, et al. (1999) "A cell line-based neutralization assay for primary human immunodeficiency virus type 1 isolates that use either the CCR5 or the CXCR4 coreceptor", J. Virol. 73(11):8966-8974.

Vicenzi, et al. (1999) "Envelope-dependent restriction of human immunodeficiency virus type 1 spreading in CD$(+) T lymphocytes: R5 but not X4 viruses replicate in the absence of T-cell receptor restimulation", J. Virol. 73(9):7515-23.

Wang, et al. (2000) "Molecular and biological interactions between two HIV-1 strains from a coinfected patient reveal the first evidence in favor of viral synergism" Virology 274(1):105-119.

Zhang, et al. (1999) "Will multiple coreceptors need to be targeted by inhibitors of human immunodeficiency virus type 1 entry", J. Virol. 73(4):3443-8.

Penn, et al., "CXCR4 utilization is sufficient to trigger CD4+ T cell depletion in HIV-1-infected human lymphoid tissue", Proceedings of the National Academy of Sciences of the United States of America, vol. 96, No. 2(Jan. 19, 1999), pp. 663-668.

Overbaugh, et al., "Distinct but related human immunodeficiency virus type 1 variant populations in genital secretions and blood", AIDS Research and Human Retroviruses, vol. 12, No. 2(Jan. 20, 1996), pp. 107-115. Abstract Only.

Bazan, et al., Patterns of CCR5, CXCR4, and CCR3 Usage by Envelope Glycoproteins from Human Immunodeficiency Virus Type 1 Primary Isolates. Journal of Virology, May 1998, vol. 72, No. 5, p. 4485-4491.

Ansari, et al., "Implications of X4 tropic virus detection before HAART and disease progression", AIDS (2008) vol. 22, pp. 533-534.

Burger and Hoover, HIV-1 Tropism, Disease Progression, and Clinical Management, JID (2008) vol. 198, pp. 1095-1097.

Cardozo, et al., Structural Basis for Coreceptor Selectivity by the HIV Type 1 V3 Loop, Aids Research and Human Retrovirus (2007) vol. 23, pp. 415-426.

Daar, et al. "Baseline HIV Type 1 Coreceptor Tropism Predicts Disease Progression", Clinical Infectious Diseases (2007) vol. 45, pp. 643-649.

De Mendoza, et al., "Prevalence of X4 Tropic Viruses in Patients Recently Infected with HIV-1 and Lack of Association with Transmission of Drug Resistance", Journal of Antimicrobial Chemotherapy (2007) vol. 59, pp. 698-704.

Goetz, et al., "Relationship between HIV coreceptor tropism and disease progression in persons with untreated chronic HIV infection", J Acquir Immune Defic Syndr (2009) vol. 50, No. 3, pp. 259-266.

McCarthy, et al., "Comparison of Phenotypic (Trofile*) and Genotypic SensiTrop II) Assays to Determine HIV Tropism in Treatment-Naïve Subjects" Presented at the 16th Conference on Retroviruss and Opportunistic Infections, Montreal, Canada, Feb. 8-11, 2009.

Pastore, et al., "Intrinsic Obstacles to Human Immunodeficiency Virus Type 1 Coreceptor Switching" Journal of Virology (2004) vol. 78, No. 14, pp. 7565-7574.

Shepard, et al., "Emergence and Persistence of CXCR4-Tropic HIV-1 in a Population of Men from the Multicenter AIDS Cohort Study" JID (2008) vol. 198, pp. 1104-1112.

Weiser, et al., "HIV-1 coreceptor usage and CXCR4-specific viral load predict clinical disease progression during combination antiretroviral therapy" AIDS (2008) vol. 22, pp. 469-479.

* cited by examiner

SEQUENCE LISTING

<160> NUMBER OF SEQ ID NOS: 35

<210> SEQ ID NO 1
<211> LENGTH: 35
<212> TYPE: PRT
<213> ORGANISM: Human immunodeficiency virus type 1

<400> SEQUENCE: 1

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Ile Gly Asp Ile Arg Gln
            20                  25                  30

Ala Tyr Cys
        35

<210> SEQ ID NO 2
<211> LENGTH: 35
<212> TYPE: PRT
<213> ORGANISM: Human immunodeficiency virus type 1

<400> SEQUENCE: 2

Cys Ile Arg Pro Asn Asn Asn Thr Arg Thr Ser Ile Arg Ile Gly Pro
1               5                   10                  15

Arg Gln Ala Phe Tyr Ala Thr Gly Asn Ile Ile Gly Asp Ile Arg Gln
            20                  25                  30

Ala Tyr Cys
        35

<210> SEQ ID NO 3

```
<211> LENGTH: 35
<212> TYPE: PRT
<213> ORGANISM: Human immunodeficiency virus type 1

<400> SEQUENCE: 3

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Val Gly Asp Ile Arg Gln
            20                  25                  30

Ala Tyr Cys
        35

<210> SEQ ID NO 4
<211> LENGTH: 27
<212> TYPE: PRT
<213> ORGANISM: Human immunodeficiency virus type 1

<400> SEQUENCE: 4

Arg Lys Ser Val His Ile Gly Pro Gly Gln Ala Phe Tyr Ala Thr Gly
1               5                   10                  15

Asp Ile Ile Gly Asn Ile Arg Lys Ala His Cys
            20                  25

<210> SEQ ID NO 5
<211> LENGTH: 35
<212> TYPE: PRT
<213> ORGANISM: Human immunodeficiency virus type 1

<400> SEQUENCE: 5

Cys Thr Arg Pro Asn Asn Asn Thr Arg Lys Ser Val His Ile Gly Pro
1               5                   10                  15

Gly Gln Ala Phe Tyr Ala Thr Gly Asp Ile Ile Gly Asn Ile Arg Lys
            20                  25                  30

Ala His Cys
        35

<210> SEQ ID NO 6
<211> LENGTH: 35
<212> TYPE: PRT
<213> ORGANISM: Human immunodeficiency virus type 1

<400> SEQUENCE: 6

Cys Thr Arg Pro Asn Asn Asn Thr Arg Lys Ser Val His Ile Gly Pro
1               5                   10                  15

Gly Gln Ala Phe Tyr Ala Thr Gly Asp Ile Ile Gly Asn Ile Arg Gln
            20                  25                  30

Ala His Cys
        35

<210> SEQ ID NO 7
<211> LENGTH: 35
<212> TYPE: PRT
<213> ORGANISM: Human immunodeficiency virus type 1

<400> SEQUENCE: 7

Cys Thr Arg Pro Asn Asn Asn Thr Arg Lys Ser Val His Ile Gly Pro
1               5                   10                  15

Gly Gln Ala Phe Tyr Ala Thr Gly Asp Ile Ile Gly Asn Met Arg Lys
            20                  25                  30

Ala His Cys
        35
```

<210> SEQ ID NO 8
<211> LENGTH: 35
<212> TYPE: PRT
<213> ORGANISM: Human immunodeficiency virus type 1

<400> SEQUENCE: 8

Cys Thr Arg Pro Ile Asn Asn Arg Arg Lys Ser Ile His Met Gly Pro
1               5                   10                  15

Gly Gln Ala Phe Tyr Gly Thr Asp Asp Ile Ile Gly Asp Ile Arg Lys
            20                  25                  30

Ala Arg Cys
        35

<210> SEQ ID NO 9
<211> LENGTH: 36
<212> TYPE: PRT
<213> ORGANISM: Human immunodeficiency virus type 1

<400> SEQUENCE: 9

Cys Thr Arg Pro Ser Asn Asn Arg Arg Lys Ser Ile His Lys Gly Asp
1               5                   10                  15

Gln Asp Lys His Ser Met Glu His Asp Asp Val Ile Gly Asp Ile Arg
            20                  25                  30

Lys Ala Arg Cys
            35

<210> SEQ ID NO 10
<211> LENGTH: 35
<212> TYPE: PRT
<213> ORGANISM: Human immunodeficiency virus type 1

<400> SEQUENCE: 10

Cys Thr Arg Pro Ile Asn Asn Arg Arg Lys Ser Ile His Ile Gly Pro
1               5                   10                  15

Gly Gln Ala Phe Tyr Gly Thr Asp Asp Ile Ile Gly Asp Ile Arg Gln
            20                  25                  30

Ala His Cys
        35

<210> SEQ ID NO 11
<211> LENGTH: 34
<212> TYPE: PRT
<213> ORGANISM: Human immunodeficiency virus type 1

<400> SEQUENCE: 11

Cys Ile Arg Pro Asn Asn Asn Thr Arg Gln Ser Val His Ile Gly Pro
1               5                   10                  15

Gly Gln Ala Leu Tyr Thr Thr Glu Ile Ile Gly Asp Ile Arg Lys Ala
            20                  25                  30

His Cys

<210> SEQ ID NO 12
<211> LENGTH: 35
<212> TYPE: PRT
<213> ORGANISM: Human immunodeficiency virus type 1

<400> SEQUENCE: 12

Cys Thr Arg Pro Asn Asn Asn Thr Ile Thr Ser Ile Arg Ile Gly Pro
1               5                   10                  15

Gly Gln Ala Phe Tyr Ala Thr Gly Ser Ile Ile Gly Asn Ile Arg Gln
            20                  25                  30

```
Ala His Cys
        35

<210> SEQ ID NO 13
<211> LENGTH: 35
<212> TYPE: PRT
<213> ORGANISM: Human immunodeficiency virus type 1

<400> SEQUENCE: 13

Cys Thr Arg Pro Asn Asn Asn Thr Ile Thr Ser Ile Arg Ile Gly Pro
1               5                   10                  15

Gly Gln Ala Phe Tyr Ala Thr Gly Ser Ile Ile Gly Asn Thr Arg Gln
            20                  25                  30

Ala His Cys
        35

<210> SEQ ID NO 14
<211> LENGTH: 35
<212> TYPE: PRT
<213> ORGANISM: Human immunodeficiency virus type 1

<400> SEQUENCE: 14

Cys Thr Arg Pro Asn Asp Asn Ile Arg Lys Ser Val His Ile Gly Pro
1               5                   10                  15

Gly Gln Ala Phe Tyr Ala Thr Gly Asp Ile Ile Gly Asp Ile Arg Arg
            20                  25                  30

Ala His Cys
        35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcttaggca tctcctatgg caggaagaa                                            29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcttaggca tctcctatgg caggaagaa                                            29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agaaagagca gaagacagtg gcaatga                                              27

<210> SEQ ID NO 18
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcccttcca gtcccccctt ttcttttta                                           28

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcacagtaca atgtacacat g                                                   21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaagaccca acaacaatac a                                                   21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtattgttg ttgggtcttg t                                                   21

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Gly or Ser
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (20)
<223> OTHER INFORMATION: Asp or Glu

<400> SEQUENCE: 22
```

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)
<223> OTHER INFORMATION: Lys, His, or Arg
<220> FEATURE:
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (20)
<223> OTHER INFORMATION: Asp or Glu

<400> SEQUENCE: 23

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)
<223> OTHER INFORMATION: Any naturally occurring amino acid other than
      Lys, His or Arg
<220> FEATURE:
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (20)
<223> OTHER INFORMATION: Asp, Glu, Lys, His or Arg

<400> SEQUENCE: 24

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

```
<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)
<223> OTHER INFORMATION: Lys, His or Arg
<220> FEATURE:
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (20)
<223> OTHER INFORMATION: Lys, His or Arg

<400> SEQUENCE: 25

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

<210> SEQ ID NO 26
<211> LENGTH: 35
<212> TYPE: PRT
<213> ORGANISM: Human immunodeficiency virus type 1

<400> SEQUENCE: 26

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Ile Gly Gly Ile Arg Gln
            20                  25                  30

Ala Tyr Cys
        35

<210> SEQ ID NO 27
<211> LENGTH: 35
<212> TYPE: PRT
<213> ORGANISM: Human immunodeficiency virus type 1

<400> SEQUENCE: 27

Cys Thr Arg Pro Asn Asn Asn Thr Arg Lys Ser Val His Ile Gly Leu
1               5                   10                  15

Gly Gln Ala Phe Tyr Ala Thr Gly Asp Ile Ile Gly Asn Ile Arg Lys
            20                  25                  30

Ala His Cys
        35

<210> SEQ ID NO 28
<211> LENGTH: 35
<212> TYPE: PRT
<213> ORGANISM: Human immunodeficiency virus type 1

<400> SEQUENCE: 28
```

Cys Thr Arg Pro Asn Asn Asn Thr Arg Lys Ser Val His Ile Gly Pro
1               5                   10                  15

Gly Gln Ala Phe Tyr Ala Thr Gly Asp Ile Leu Gly Asn Ile Arg Gln
            20                  25                  30

Ala His Cys
        35

<210> SEQ ID NO 29
<211> LENGTH: 35
<212> TYPE: PRT
<213> ORGANISM: Human immunodeficiency virus type 1

<400> SEQUENCE: 29

Cys Thr Arg Pro Asn Asn Asn Thr Arg Lys Ser Val His Ile Gly Pro
1               5                   10                  15

Gly Gln Ala Phe Tyr Ala Thr Gly Asp Ile Ile Gly Asp Ile Arg Gln
            20                  25                  30

Ala Tyr Cys
        35

<210> SEQ ID NO 30
<211> LENGTH: 35
<212> TYPE: PRT
<213> ORGANISM: Human immunodeficiency virus type 1

<400> SEQUENCE: 30

Cys Thr Arg Pro Asn Asn Asn Thr Lys Lys Ser Val His Ile Gly Pro
1               5                   10                  15

Gly Gln Ala Phe Tyr Ala Thr Gly Asp Ile Ile Gly Asp Ile Arg Gln
            20                  25                  30

Ala Tyr Cys
        35

<210> SEQ ID NO 31
<211> LENGTH: 35
<212> TYPE: PRT
<213> ORGANISM: Human immunodeficiency virus type 1

<400> SEQUENCE: 31

Cys Thr Arg Pro Asn Asp Asn Ile Arg Lys Arg Val His Ile Gly Pro
1               5                   10                  15

Gly Gln Ala Phe Tyr Ala Thr Gly Asp Val Ile Gly Asp Ile Arg Arg
            20                  25                  30

Ala His Cys
        35

<210> SEQ ID NO 32
<211> LENGTH: 35
<212> TYPE: PRT
<213> ORGANISM: Human immunodeficiency virus type 1

<400> SEQUENCE: 32

Cys Thr Arg Pro Ile Asn Asn Arg Arg Lys Ser Ile His Ile Gly Pro
1               5                   10                  15

Gly Gln Ala Phe Tyr Gly Thr Asp Asp Ile Ile Gly Asp Ile Arg Gln
            20                  25                  30

Ala His Cys
        35

<210> SEQ ID NO 33
<211> LENGTH: 35

```
<212> TYPE: PRT
<213> ORGANISM: Human immunodeficiency virus type 1

<400> SEQUENCE: 33

Cys Thr Arg Pro Ser Asn Asn Arg Arg Lys Ser Ile His Met Gly Pro
1               5                   10                  15

Gly Gln Ala Phe Tyr Gly Thr Asp Asp Ile Ile Gly Gly Ile Arg Lys
            20                  25                  30

Ala Arg Cys
        35

<210> SEQ ID NO 34
<211> LENGTH: 35
<212> TYPE: PRT
<213> ORGANISM: Human immunodeficiency virus type 1

<400> SEQUENCE: 34

Cys Thr Arg Pro Ser Asn Asn Arg Arg Lys Ser Ile His Met Gly Pro
1               5                   10                  15

Gly Gln Ala Phe Tyr Gly Thr Asp Asp Ile Ile Gly Asp Ile Arg Lys
            20                  25                  30

Ala Arg Cys
        35

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (20)
<223> OTHER INFORMATION: Variable amino acid
<220> FEATURE:
<223> OTHER INFORMATION: See specification as filed for detailed
      description of substitutions and preferred embodiments

<400> SEQUENCE: 35

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20
```

ANALYSIS OF HIV-1 CORECEPTOR USE IN THE CLINICAL CARE OF HIV-1-INFECTED PATIENTS

RELATED APPLICATIONS/PATENTS & INCORPORATION BY REFERENCE

This application is a divisional application of U.S. application Ser. No. 10/695,846, now allowed, filed Oct. 29, 2003 now U.S. Pat. No. 7,294,458, which is a divisional application of U.S. application Ser. No. 09/963,064, filed Sep. 25, 2001 and issued as U.S. Pat. No. 6,727,060 on Apr. 27, 2004, and which claims priority to U.S. Provisional Application Ser. No. 60/235,671, filed Sep. 26, 2000, and U.S. Provisional Patent Application Ser. No. 60/282,354, filed Apr. 6, 2001.

STATEMENT OF RIGHTS TO INVENTIONS MADE UNDER FEDERALLY SPONSORED RESEARCH

This work was supported by the government, in part, by Grant U01A135004 from the National Institute for Allergy and Infectious Diseases and a National Research Service Award (1F32HD08478-01) from the National Institute of Child Health and Human Development. The government may have certain rights to this invention.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

FIELD OF THE INVENTION

The present invention relates to a diagnostic method to monitor coreceptor use in treatment of human immunodeficiency virus (HIV, or "an AIDS virus") infection. This method can be used to assist in selecting antiretroviral therapy and to improve predictions of disease prognosis. The present invention further relates to a diagnostic method to monitor the suppression of CXCR4-specific strains in HIV infected individuals undergoing antiretroviral therapy. Other aspects of the invention are described in or are obvious from the following disclosure (and within the ambit of the invention).

BACKGROUND OF THE INVENTION

HIV uses a receptor-mediated pathway in the infection of host cells. HIV-1 requires contact with two cell-surface receptors to gain entry into cells and initiate infection; CD4 is the primary receptor. CXCR4 and CCR5, members of the chemokine receptor family of proteins, serve as secondary coreceptors for HIV-1 isolates that are tropic for T-cell lines or macrophages, respectively. Deng et al. (1996) Nature 381: 661-6; Doranz et al. (1996) Cell 86:1149-59; and Berger et al. (1998) Nature 391:240. CXCR4 or CCR5, in conjunction with CD4, form a functional cellular receptor for entry of certain strains of HIV into cells. Reports indicated that the viral envelope glycoprotein gp120 interacts directly with chemokine receptors generally at a step following CD4 binding. Lapham et al. (1996) Science 274:602-605; Moore (1997) Science 276:51; Wu et al. (1996) Nature 384:179-183; and Hesselgesser et al. (1997) Current Biology 7:112-121. Envelope variants will selectively interact with either CXCR4 or CCR5.

HIV-1 strains transmitted in vivo generally use CCR5 (CCR5 viruses). Fenyo et al. (1998) Nature 391:240; Samson et al. (1996) Nature 382:722-5; Shankarappa et al. (1999) J. Virol. 73:10489-502; and Scarlatti et al. (1997) Nature Med. 3:1259-65. These viruses typically infect macrophages and primary CD4+ lymphocytes, and do not form syncytia in vitro. Björndal et al. (1997) J. Virol. 71:7478-87. These viruses are said to be macrophage tropic (M-tropic). After primary HIV-1 infection, viral populations are usually characterized by molecular heterogeneity. Shankarappa et al. (1999); and Glushakova et al. (1999) J. Clin. Invest. 104:R7-R11.

Years after chronic infection is established, strains using CXCR4 emerge in ~50% of infected individuals. Berger et al. (1998); Scarlatti et al. (1997); Koot et al. (1993); and Connor et al. (1997) J. Exp. Med. 185:621-8. CXCR4 strains not only infect primary T-lymphocytes but also replicate in T-cell lines and induce syncytia. Björndal et al. (1997). These viruses are said to be T-cell tropic (T-tropic). This difference in cell tropism correlates with disease progression. During HIV infection, strains isolated from individuals early in the course of their infection are usually M-tropic, while viruses isolated from approximately 50% of individuals with advanced immunodeficiency also include viruses that are T-tropic.

The finding that change from M- to T-tropic viruses over time in infected individuals correlates with disease progression suggested that the ability of the viral envelope to interact with CXCR4 represents an important feature in the pathogenesis of immunodeficiency and the development of full blown Acquired Immunodeficiency Syndrome (AIDS).

CXCR4 strains have now been shown to have a striking influence on HIV-1 disease progression. Cytopathicity toward the general CD4+ T cell population in lymphoid tissue is associated with the use of CXCR4. Glushakova et al. (1999). The emergence of CXCR4 virus is predictive of rapid depletion of CD4+ cells and acceleration of HIV-1 disease progression. Berger et al. (1998); Scarlatti et al. (1997); and Connor et al. (1997). (1997). A recent analysis of HIV-1 coreceptor use in infected individuals suggested that the rapid CD4+ cell decline is related to the ability of CXCR4 viruses to infect an expanded spectrum of crucial target cells as compared to CCR5 strains. Blaak et al. (2000) Proc. Natl. Acad. Sci. USA 97:1269-74. In vitro results suggest that selective blockade of CXCR4 receptors may prevent the switch from the less pathogenic CCR5 strains to the more pathogenic CXCR4 strains. Este et al. (1999) J. Virol. 73:5577-85. Coreceptor use plays a critical role in viral tropism, pathogenesis, and disease progression. Thus, a diagnostic method for use in detecting CXCR4 isolates and/or monitoring shifts in coreceptor use would be beneficial for predicting disease progression over time.

Treatment of infected individuals with highly active antiretroviral therapy (HAART) has led to a dramatic decline in both HIV-1-related illness and death. Palella et al. (1998) N. Engl. J. Med. 338:853-60. Early clinical trials demonstrated a reduction of plasma HIV-1 RNA loads to undetectable levels in the majority of treated individuals. Hammer et al. (1997) N. Engl. J. Med. 337:725-33; and Autran et al. (1997) Science 277:112-6. Subsequent studies, however, showed more limited success in achieving and maintaining viral suppression. Deeks et al. (2000) J. Inf. Dis. 181:946-53; and Mezzaroma et al. (1999) Clin. Inf. Dis. 29:1423-30. Yet many patients experienced immunologic and clinical responses to HAART without sustained suppression of plasma viremia. Deeks et al. (2000); and Mezzaroma et al. (1999).

The emergence of viral variants in connection with the failure of HAART may be associated with modified expression of the host determinants of viral tropism, including CCR5 and CXCR4. In comparison to pretherapy determinations, expression of CXCR4 was significantly increased, and CCR5 decreased, following three months of an anti-viral regimen. Giovannetti et al. (1999) Clin. Exp. Immunol. 118: 87-94. Changes in coreceptor expression occurred in association with a decrease in viral load and T cell activation, and an increase in naive and memory T cells signifying peripheral redistribution of T cell compartments. In a separate study, HAART was reported to reduce the expression of CXCR4 and CCR5 in lymphoid tissue. Andersson et al. (1998) AIDS 12:F123-9. These studies did not address coreceptor usage in patients undergoing HAART. The effects of HAART on coreceptor usage by viral populations were heretofore unknown.

OBJECTS AND SUMMARY OF THE INVENTION

Unexpectedly, it has now been shown that in patients undergoing HAART after the CXCR4-specific strains have emerged, the predominant populations of virus can be shifted back to CCR5-mediated entry as a result of the preferential suppression of X4 strains of HIV-1. Thus, a diagnostic method for use in monitoring shifts in coreceptor use would be beneficial for measuring the therapeutic efficacy of various HIV treatment regimes, such as HAART.

The correlation between CXCR4-specific strains and rapid disease progression indicates that a diagnostic method would be useful to monitor the presence of CXCR4-specific strains and shifts in coreceptor use associated with HIV disease progression. Application of the diagnostic method allows more accurate predictions of disease prognosis over time.

The effect of HAART on coreceptor use by populations of virus has not heretofore been quantitatively studied. Herein, it is shown that in patients undergoing combination antiretroviral therapy, including HAART, the predominant populations of virus can be shifted back to CCR5-mediated entry once the CXCR4-specific strains have emerged.

Therefore, a diagnostic method is also useful to monitor the presence of CXCR4-specific strains and changes in HIV coreceptor use in patients undergoing antiretroviral therapy. Application of the diagnostic method allows the effectiveness of antiretroviral therapy to be more closely monitored.

The present invention relates to a diagnostic method to determine whether CXCR4 or CCR5 isolates are present in a patient comprising assaying for coreceptor use.

The present invention further relates to a diagnostic method to determine whether CXCR4 or CCR5 strains are present in a patient comprising transforming cells with an HIV envelope gene variant cloned from an infected patient, selectively fusing the cells with an indicator cell line expressing an HIV envelope-compatible coreceptor, and assaying for fusion.

The present invention further relates to a diagnostic method to determine whether CXCR4 or CCR5 strains are present in a patient comprising obtaining patient-derived virus and assaying the isolates for coreceptor use.

The present invention further relates to a diagnostic method to monitor changes in coreceptor use associated with changes in HIV disease progression.

The present invention further relates to a diagnostic method to monitor changes in coreceptor use associated with changes in HIV disease progression comprising transforming cells with an HIV envelope gene variant cloned from an infected patient, selectively fusing the cells with an indicator cell line expressing an HIV envelope-compatible coreceptor, and assaying for fusion.

The present invention further relates to a diagnostic method to monitor changes in coreceptor use associated with changes in HIV disease progression comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression.

The present invention further relates to a diagnostic method to monitor changes in coreceptor use associated with changes in HIV disease progression comprising determining CXCR4 coreceptor use, CCR5 coreceptor use, and a ratio of HIV using the CXCR4 coreceptor compared to HIV using the CCR5 coreceptor.

The present invention further relates to a diagnostic method to monitor changes in coreceptor use associated with changes in HIV disease progression by obtaining patient-derived virus and deriving biological clones therefrom, assaying the clones for coreceptor use, and applying a method of quantitating the proportion of virus that uses each coreceptor.

The present invention further relates to a diagnostic method to determine whether CXCR4 or CCR5 strains are present in patients infected with HIV undergoing antiretroviral therapy.

The present invention further relates to a diagnostic method to determine whether CXCR4 or CCR5 strains are present in patients infected with HIV undergoing antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention further relates to a diagnostic method to determine whether CXCR4 or CCR5 strains are present in patients infected with HIV undergoing antiretroviral therapy comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression before and/or after initiating antiretroviral therapy.

The present invention further relates to a diagnostic method to determine whether CXCR4 or CCR5 strains are present in patients infected with HIV undergoing antiretroviral therapy comprising obtaining patient-derived virus and assaying the virus for coreceptor use before and/or after initiating antiretroviral therapy.

The present invention further relates to a diagnostic method to monitor the suppression of CXCR4-specific strains in patients infected with HIV undergoing antiretroviral therapy.

The present invention further relates to a diagnostic method to monitor the suppression of CXCR4-specific strains in patients infected with HIV undergoing antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention further relates to a diagnostic method to monitor the suppression of CXCR4-specific strains in patients infected with HIV undergoing antiretroviral therapy comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression before and/or after initiating antiretroviral therapy.

The present invention further relates to a diagnostic method to monitor the suppression of CXCR4-specific strains in patients infected with HIV undergoing antiretroviral therapy comprising obtaining patient-derived virus and assaying the virus for coreceptor use before and/or after initiating antiretroviral therapy.

The present invention further relates to a diagnostic method to monitor the suppression of CXCR4-specific strains in patients infected with HIV undergoing antiretroviral therapy comprising determining CXCR4 coreceptor use, CCR5 coreceptor use, and a ratio of HIV using the CXCR4 coreceptor compared to HIV using the CCR5 coreceptor before and/or after initiating antiretroviral therapy.

The present invention further relates to a diagnostic method to monitor the suppression of CXCR4-specific strains in patients infected with HIV undergoing antiretroviral therapy comprising obtaining primary viral isolates and deriving biological clones therefrom, assaying the clones for coreceptor use, and applying a method for quantitating the proportion of virus in a primary isolate that uses each coreceptor before and/or after initiating antiretroviral therapy.

The present invention further relates to a diagnostic method to monitor the suppression of CXCR4-specific strains in patients infected with HIV undergoing antiretroviral therapy comprising determining the sequence of HIV envelope gene before and/or after initiating antiretroviral therapy.

These and other objects and embodiments are described in or are obvious from and within the scope of the invention, from the following Detailed Description.

BRIEF DESCRIPTION OF THE FIGURES

In the following Detailed Description and Examples reference will be made to the accompanying drawings, incorporated herein by reference.

FIG. 1. depicts the effect of combination antiretroviral therapy on HIV-1 coreceptor use over time in representative study subjects. Patients 1, 2, 6, 8, and 10 received new, combination therapy and Patient 13 remained untreated. Arrows note the first time during the study period that a new combination of antiretroviral drugs was initiated. Two arrows appear if a patient received a two drug regimen first, then HAART. The duration of treatment with each agent is indicated. Drugs are abbreviated as follows: AZT, zidovudine; 3TC, lamivudine; Rit, ritonavir; Ind, indinavir; Saq, saquinavir; d4T, stavudine; Nel, nelfinavir; ddI, didanosine; ddC, zalcitabine; and Nev, nevirapine.

FIG. 2. depicts the dynamics of the shift in coreceptor utilization immediately following initiation of HAART.

FIG. 3. depicts an example of a template set-up for a PE2400 PCR tray-retainer.

FIG. 4. depicts an example of a pattern produced by gel analysis based on an original RT layout, for use in selecting samples to be cloned/sequenced.

DETAILED DESCRIPTION

The present invention relates to a diagnostic method to determine whether CXCR4 or CCR5 strains are present in a patient infected with HIV.

The present invention further relates to a diagnostic method to determine whether CXCR4 or CCR5 strains are present in a patient comprising transforming cells with an HIV envelope gene cloned from an infected patient, selectively fusing the cells with an indicator cell line expressing an HIV envelope-compatible coreceptor, and assaying for fusion. Cell surface envelope protein variants will selectively interact with either CCR5 or CXCR4. Fusion only occurs when an envelope protein interacts with a compatible coreceptor present on the surface of indicator cells. Cells expressing a particular envelope gene will fuse with either CCR5 or CXCR4 indicator cells, depending on the patient's envelope gene specificity. Therefore, whether fusion occurs with either CCR5 or CXCR4 indicator cells will indicate coreceptor usage.

A patient or subject can be any animal, preferably a mammal, and even more preferably a human, infected with HIV. The infectious AIDS virus can be, but is not limited to, HIV-1 and HIV-2.

An indicator cell line is a cell line comprising the CD4 receptor and a coreceptor or functional fragments thereof, susceptible to infection with HIV. Preferably the coreceptor is CXCR4 or CCR5. An indicator cell line can be, for example, HOS-CD4.CCR5 and HOS-CD4.CXCR4 (Deng et al. (1996); and Equils et al. (2000) J. Inf. Dis. 182:751-757), available from the AIDS Research and Reference Reagent Program Catalog. Other cell lines available from this catalog that are suitable for use as indicator cell lines include U373-MAGI (Fred Hutchinson Research Cancer Center); 3T3.T4, GHOST and U87.CD4 (New York University Medical Center). An indicator cell line can be any known in the art, such as described in Glushakova et al. (1999); and Dreyer et al. (1999). Although engineered primarily to screen HIV strains for drug sensitivity, the indicator cell lines described in WO 99/67429 are also also suitable for use as indicator cell lines.

An indicator cell line can be constructed by methods known in the art. Nucleic acids encoding HIV receptors or coreceptors, such as CD4, CXCR4 and/or CCR5, or functional fragments thereof capable of effecting receptor binding, can be cloned into recombinant vectors and introduced into cells of choice in vitro. HIV receptors and coreceptors or fragments thereof can be expressed by the recombinant vectors in cells of choice. Methods for generation and use of recombinant vectors in vitro are well known in the art. See Sambrook, Fritsch and Maniatis, Molecular Cloning, A Laboratory Manual, 2nd Ed., Cold Spring Harbor Laboratory Press, 1989 (e.g., procedures for isolating DNA, constructing recombinant vectors, transfecting and transforming cells and producing heterologous peptides).

The term "or (a) fragment(s) thereof" as employed in the present invention and in context with polypeptides of the invention, comprises specific peptides, amino acid stretches of the polypeptides as disclosed herein. It is preferred that said "fragment(s) thereof" is/are functional fragment(s). The term "functional fragment" denotes a part of the above identified polypeptide of the invention which fulfils, at least in part, physiologically and/or structurally related activities of the polypeptide of the invention. It is also envisaged that the fragments, like the full-length polypeptides, can distinguish between HIV strains in effecting binding. The polypeptides of the present invention can be recombinant polypeptides expressed in eukaryotic cells, like mammalian cells.

Generally, recombinant DNA technology has enabled the expression of foreign (heterologous) proteins in cell lines of choice. In this process, a vector containing genetic material directing a cell to produce a protein encoded by a portion of a heterologous DNA sequence is introduced into the host, and the transformed host cells can be fermented, cultured or otherwise subjected to conditions which facilitate the expression of the heterologous DNA, leading to the formation of large quantities of the desired protein. Plasmids are extensively used as vectors to clone DNA molecules. Most plasmid vectors are made by taking DNA from a variety of replicons (plasmids, bacteriophage chromosomes and bacterial chromosomes) and joining the DNA together (using restriction enzymes and DNA ligase) to form a plasmid that has an origin of replication, a selection marker (usually an antibiotic-resistance gene) and a promoter for expressing genes of interest in the required host cell. A vector can be, for example, as in U.S. Pat. Nos. 5,990,091 and 6,004,777, and as in PCT/US00/04203.

Furthermore, the recombinant vector can, in addition to the nucleic acid sequences of the invention (e.g. those encoding HIV receptors or coreceptors or functional fragments thereof), comprise expression control elements, allowing proper expression of the coding regions in suitable hosts. Such control elements are known in the art and can include a promoter, a splice cassette, translation initiation codon, translation and insertion site for introducing an insert into the vector. Preferably, the nucleic acid molecule is operatively linked to expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements can include transcriptional as well as translational enhancers, and/or naturally-associated or heterologous promoter regions. Possible regulatory elements permitting expression in for example mammalian cells comprise the CMV-HSV thymidine kinase promoter, SV40, RSV-promoter (Rous sarcoma virus), human elongation factor 1$\alpha$-promoter, aPM-I promoter (Schaffer et al. (1999) Biochem. Biophys. Res. Commun. 260:416-425), or inducible promoter(s), like, metallothionein or tetracyclin, or enhancers, like CMV enhancer or SV40-enhancer. For the expression in prokaryotic cells, a multitude of promoters including, for example, the tac-lac-promoter or the trp promoter, has been described. Besides elements that are responsible for the initiation of transcription, such regulatory elements can also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), Casper, Casper-HS43, pUAST, or prokaryotic expression vectors, such as lambda gt11.

Furthermore, depending on the expression system leader sequences capable of directing the polypeptide to a cellular compartment can be added to the coding sequence of the nucleic acid molecules of the invention and are well known in the art. The leader sequence(s) is assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization of expressed recombinant products. Once the vector has been incorporated into the appropriate cell line, the cells are maintained under conditions suitable for high level expression of the nucleotide sequences.

A cell can be transfected or transformed with a recombinant vector or plasmid. Methods of transformation and transfection are well known in the art. The transformed cells can be grown in fermentors and cultured according to techniques known in the art to achieve optimal cell growth. The resulting transformed or transfected cell lines are genetically modified with a nucleic acid molecule according to the invention or with a vector comprising such a nucleic acid molecule. The term "genetically modified" means that the cell comprises in addition to its natural genome a nucleic acid molecule or vector according to the invention which was introduced into the cell or host or into one of its predecessors/parents. The nucleic acid molecule or vector can be present in the genetically modified cell either as an independent molecule outside the genome, preferably as a molecule that is capable of replication, or it can be stably integrated into the genome of the cell.

The present invention can utilize any suitable prokaryotic or eukaryotic cell to construct an indicator cell line. Suitable prokaryotic cells are those generally used for cloning like *Escherichia coli* or *Bacillus subtilis*. Eukaryotic cells comprise, for example, fungal or animal cells, and are preferable for constructing an indicator cell line. Animal cells are preferably used for conducting the specificity assay. Suitable animal cells are, for instance, insect cells, vertebrate cells, preferably mammalian cells, such as e.g. GHOST, CHO, Hela, NIH3T3, MOLT-4, Jurkat, K562, HepG2, 3T3-L1 (and derivatives thereof), HIB-1B (Villena et al. (1998) Biochem. J. 331:121-127), HEK 293, PAZ6 (Strobel et al. (1999) Diabetologia 42:527-533). Further suitable cell lines known in the art are obtainable from cell line depositories, like the American Type Culture Collection (ATCC) and the AIDS Research and Reference Reagent Program Catalog. For example, HL3T1 and HeLa CD4+ (NIH) and HeLa T4+ (Columbia University) cell lines are available through the catalog and are easily adaptable for use in constructing an indicator cell line. Derivation of primary cells from an animal, preferably a mammal, and even more preferable a human, can also be undertaken for the purposes of establishing a suitable cell line.

Preferably, the cell transformed with the receptor/coreceptor encoding vector of the invention is a blood cell, such as a macrophage or T cell, or an immortalized cell line derived therefrom.

Cloning strategies for isolating envelope genes of interest are well known in the art. See Sambrook, Fritsch and Maniatis, Molecular Cloning, A Laboratory Manual, 2nd Ed., Cold Spring Harbor Laboratory Press, 1989. Advantageously, envelope gene sequences can be obtained from a variety of patient tissues, including blood and mucosal tissues. High fidelity cloning of the samples above can be achieved by routine performance of multiple long RT-PCR reactions on limiting dilutions of RNA, followed by multiple PCR's on cDNAs obtained from each RT reaction. Performance of multiple PCR's on each cDNA preparation increases the likelihood of amplifying a different HIV-1 RNA species. These measures also decrease the chance of recombination.

Clinical specimens comprising tissues and/or fluids from HIV-infected patients can be utilized for cloning envelope genes of interest. Advantageously, patient-derived virus can be obtained from sites in addition to peripheral blood, particularly those sites from which cultured virus cannot be obtained. For example, while circulating macrophages and CD4+ T cells are the dominant reservoir of HIV-1, viral populations distinct from those in the peripheral blood exist in many tissue reservoirs, including the genital mucosa and lymphoid tissue.

Determination of cell fusion can be carried out using a variety of assays. The assay for cell fusion can be carried out, for example, with the use of an inducible reporter gene construct. Preferably, the inducible reporter gene construct is activated upon fusion with a cell containing a suitable transcriptional activator and/or transcription factor. A Tat-inducible reporter gene construct can be utilized, comprising a reporter gene linked to an HIV-1 LTR promoter. The reporter gene construct can encode a wide variety of colormetric, enzymatic and/or fluorescent reporter genes, such as the green fluorescent protein, placental alkaline phosphatase, firefly luciferase, β-galactosidase (encoded by the lacZ gene) and chloramphenicol acetyltransferase (encoded by the CAT gene). The assay for cell fusion can also be carried out using labeled antibodies, which specifically detect HIV envelope proteins, and CXCR4 or CCR5 coreceptors on or within a fused cell. This method can be combined with cell sorting techniques, to separate populations of fused cells.

The present invention further relates to a diagnostic method to determine whether CXCR4 or CCR5 strains are present in a patient comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression. Upon fusion of cells mediated by the envelope variant-coreceptor interaction, Tat inducible reporter gene expression will be activated.

The present invention further relates to a diagnostic method to determine whether CXCR4 or CCR5 strains are present comprising obtaining patient-derived virus and assaying the virus for coreceptor use (i.e. coreceptor assay).

Patient-derived virus includes, but is not limited to, primary viral isolates, biological clones, and molecular clones. Patient-derived viruses can be obtained from clinical specimens comprising any fluid or tissue obtained from an HIV infected individual, such as peripheral blood.

Patient-derived virus can be obtained by methods known in the art. For instance, peripheral blood of HIV-infected individuals can be separated into plasma and cell components by methods known in the art. Fang et al. (1995) Proc. Natl. Acad. Sci. USA 92:12110-4. Primary viral isolates of HIV-1 can be obtained by co-culture with normal donor peripheral blood mononuclear cells (PBMCs). Fang et al. (1995). Titration of viral isolates in PBMCs can be carried out, for example, by using the methods previously described by Fang et al (1995).

Biological clones can be derived from primary isolates by methods known in the art, such as short-term limited dilution cloning. Connor et al. (1997). Quantitation of HIV-1 RNA in plasma can be carried out, for example, by using NucliSens (Organon Teknika Corp., Durham, N.C.). Quantitation methods can set a lower limit, preferably at ≦80 copies/ml.

Biological clones are applicable for determining the proportion of virus using each receptor. It is desirable to quantitate the proportion of virus using each coreceptor when rigorously comparing coreceptor use over time.

Assaying for coreceptor use can comprise inoculating indicator cell lines with primary isolates and/or biological clones (i.e. coreceptor assay) followed by determining whether infection occurred (i.e. specificity assay).

For purposes of conducting the coreceptor assay, the indicator cells can be seeded, for example, onto 12-well plates and inoculated, preferably after 12-36 hours, such as 24 hours, with a standard quantity of titered virus, preferably $10^2 TCID_{50}$ of first passage primary viral isolates or biological clones.

For purposes of conducting the coreceptor assay CCR5- and CXCR4-specific positive control viruses can be employed, such as HIV JR-FL and LAV/HTLV-IIIB. Infection with CCR5- and CXCR4-specific positive control viruses can be carried out in parallel to infection with primary isolates and/or biological clones. Uninoculated cells can be negative controls.

Prior to conducting the coreceptor assay, indicator cell lines can be tested by inoculation with duplicate primary and control isolates to eliminate the possibility of any artifacts resulting from infection via low levels of endogenous coreceptor expression.

Following the coreceptor assay, a specificity assay is conducted to determine whether infection occurred. A suitable method for determining infection of the indicator cell line can be measurement of a complex formation. The measurement of a complex formation is well known in the art and comprises, inter alia, heterogeneous and homogeneous assays. Homogeneous assays comprise assays wherein the binding partners remain in solution. Heterogeneous assays comprise assays like, inter alia, immuno assays, for example, ELISAs, RIAs, IRMAs, FIAs, CLIAs or ECLs. Such assays are, inter alia, disclosed in U.S. Pat. No. 5,854,003 or in U.S. Pat. No. 5,639,858. Specificity assays like ELISA are preferred. Any specificity or detection step of the present invention can be assisted by computer technology or other means of automation, including flow cytometry.

A suitable method for determining whether infection of the indicator cell line occurred is contacting an epitope of HIV and identifying whether binding occurs, without binding to a control. In particular, the specificity assay of the invention can be carried out by employing antibodies directed against the HIV p24 antigen, as described by Kusunoki et al. (1999) Nucleosides Nucleo. 18:1705, or by using commercial ELISA assay kits, available, for example, from NEN Life Science Products, Boston.

Therefore, the coreceptor assay of the invention can be easily performed using the disclosure herein and methods known in the art such as described herein.

The present invention yet further relates to a diagnostic method to monitor changes in coreceptor use associated HIV disease progression.

The present invention further relates to a diagnostic method to monitor changes in coreceptor use associated with HIV disease progression comprising transforming cells with an HIV envelope gene variant cloned from an infected patient, selectively fusing the cells with an indicator cell line expressing an HIV envelope-compatible coreceptor, and assaying for fusion.

The present invention further relates to a diagnostic method to monitor changes in coreceptor use associated with HIV disease progression comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression.

The present invention further relates to a diagnostic method to monitor changes in coreceptor use associated with HIV disease progression comprising determining CXCR4 coreceptor use, CCR5 coreceptor use, and a ratio of HIV using the CXCR4 coreceptor compared to HIV using the CCR5 coreceptor.

The present invention further relates to a diagnostic method to monitor changes in coreceptor use associated with HIV disease progression comprising obtaining patient-derived virus from a clinical specimen and deriving biological clones therefrom, assaying the clones for coreceptor use, and applying a method of quantitating the proportion of virus in the clinical specimen that uses each coreceptor.

In a preferred embodiment, the coreceptor assay includes quantifying the proportion of virus using each coreceptor. Quantitation can be performed in a number of ways, including determining coreceptor specificity of multiple biologic clones, preferably at least 5; determining the viral sequence of portions of the HIV envelope gene, particularly the V3 region which predicts coreceptor use; or assaying a viral primary isolate using a semiquantitative method and applying a statistical method, for example, as described herein.

Determination of the proportion of CCR5 or CXCR4 virus can be carried out by determining coreceptor specificity of multiple biologic clones. A system devised for determining coreceptor specificity through the use of an indicator cell line is provided herein above. Biologic clones derived from the patients' primary viral isolates can be assayed for coreceptor use by employing an indicator cell line, such as the HOS-CD4+ cell line.

Determination of the proportion of CCR5 or CXCR4 virus can be carried out by determining the viral sequence of portions of the HIV envelope gene, particularly the V3 region which predicts coreceptor use. The envelope protein can be gp120, gp 160 or a portion thereof. Envelope sequences are predictive of coreceptor use on the basis of the overall charge of the V3 loop and the presence of basic or acidic residues at positions 275 and 287 of the env gene. Bhattacharya et al. (1996) AIDS Res. Hum. Retrovir. 12:83-90; and Hung et al. (1999) J. Virol. 73:8216-26. An example of a system devised for determining the viral sequence of portions of the HIV envelope gene is provided herein. Reverse transcriptase polymerase chain reaction can be used to amplify the V3 region of the env gene from plasma or other body fluid. Amplified products can be sub-cloned, verified by restriction digestion, and sequenced.

It is furthermore envisaged, that the diagnostic method involves the use of micro-chips comprising nucleic acid molecules encoding a envelope protein, or a fragment thereof, preferably a V3 region fragment, on "gene chips"; or an envelope protein, or a fragment thereof, preferably a V3 region fragment, on "protein-chips" (See U.S. Pat. Nos. 6,066,454; 6,045,996; 6,043,080; 6,040,193; 6,040,138; 6,033,860; 6,033,850; 6,025,601; 6,022,963; 6,013,440; 5,968,740; 5,925,525; 5,922,591; 5,919,523; 5,889,165; 5,885,837; 5,874,219; 5,858,659; 5,856,174; 5,856,101; 5,843,655; 5,837,832; 5,834,758; 5,831,070; 5,770,722; 5,770,456; 5,753,788; 5,744,305; 5,733,729; 5,710,000; 5,631,734; 5,599,695; 5,593,839; 5,578,832; and 5,556,752). Diagnostic gene chips can comprise a collection of polypeptides that specifically detect a envelope protein, or fragments thereof, preferably V3 region fragments; or nucleic acid molecules that specifically detect a nucleic acid molecule encoding a envelope protein, or fragments thereof, preferably V3 region fragments; all of which can be used for the purposes of determining coreceptor use. The envelope protein can be gp160, gp 120, or a portion thereof.

Determination of the proportion of CCR5 or CXCR4 strains from patient-derived virus can be carried out using a quantitative statistical method. An example of a system devised for quantitation of the proportion of CCR5 and CXCR4 strains in a clinical specimen is provided herein. In this system, lambda ($\lambda$) is a continuous, nonlinear variable between one and zero derived from the results of coreceptor use by biologically and molecularly cloned virus; it describes the mixed proportion of viruses using CCR5 and CXCR4. A $\lambda$ value near one describes a population of viruses that almost all use CCR5; a value near zero describes a population that almost all use CXCR4.

More in particular, this system comprises a variable, $\lambda$, that is constructed as the proportion of strains using CCR5. Lambda=1 represents an isolate in which all strains prefer the CCR5 coreceptor but $\lambda$=0 indicates that all prefer CXCR4. Lambda values can be assessed by utilizing qualitative assay data derived from patient-derived virus and sequences of the V3 portion of the env gene in patient-derived virus. Lambda values can be constructed by relating data derived from the same patient sample by using three different analyses: biologic cloning, V3 sequencing, and semiquantitative assays of primary isolates. To construct $\lambda$ values, the proportion of biologic and, if available, molecular clones using CCR5 at each time point is calculated, then the proportion is linked to the semiquantitative coreceptor use score (− to 3+) of primary isolates obtained simultaneously. The data are transformed to approximate a Poisson distribution. Poisson regression analysis can then be performed to determine the factors associated with changes in $\lambda$ values.

The Wilcoxon Rank Sum Test can be used to make comparisons between the magnitude of log viral level, CD4+ counts, and Lambda ($\lambda$) values. Data for factors relating to changes in $\lambda$ values can be analyzed by multivariate Poisson regression. Variables can include log HIV-1 RNA levels, changes in viral levels, CD4+ cell counts, changes in CD4+ cell counts, and indicator variables for levels of antiretroviral therapy.

Application of the diagnostic methods to detect and/or monitor changes in coreceptor use is useful for predicting disease prognosis over time.

The present invention yet further relates to a diagnostic method to determine whether CXCR4-specific strains are present in patients infected with HIV undergoing antiretroviral therapy.

The present invention further relates to a diagnostic method to determine whether CXCR4 or CCR5 strains are present in patients infected with HIV undergoing antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention further relates to a diagnostic method to determine whether CXCR4 or CCR5 strains are present in patients infected with HIV undergoing antiretroviral therapy comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression before and/or after initiating antiretroviral therapy.

The present invention further relates to a diagnostic method to determine whether CXCR4-specific strains are present in HIV-infected patients receiving antiretroviral therapy comprising obtaining patient-derived virus and assaying for coreceptor use before and/or after initiating antiretroviral therapy.

The present invention yet further relates to a diagnostic method to monitor the suppression of CXCR4-specific strains in HIV-infected patients receiving antiretroviral therapy.

The present invention further relates to a diagnostic method to monitor the suppression of CXCR4-specific strains in HIV-infected patients receiving antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention further relates to a diagnostic method to monitor the suppression of CXCR4-specific strains in HIV-infected patients receiving antiretroviral therapy comprising transforming cells containing an HIV Tat-activatable reporter gene construct with an HIV envelope gene variant cloned from an infected patient, selectively fusing the cells with an indicator cell line containing a constitutively active tat gene and an HIV envelope-compatible coreceptor, and assaying for fusion by detection of reporter gene expression before and/or after initiating antiretroviral therapy.

The present invention further relates to a diagnostic method to monitor the suppression of CXCR4-specific strains in HIV-infected patients receiving antiretroviral therapy comprising determining CXCR4 coreceptor use, CCR5 coreceptor use, and a ratio of HIV using the CXCR4 coreceptor compared to HIV using the CCR5 coreceptor before and/or after initiating antiretroviral therapy.

The present invention further relates to a diagnostic method comprising obtaining patient-derived virus from a clinical specimen and deriving biological clones therefrom, assaying the clones for coreceptor use, and applying a method for quantitating the proportion of virus in the clinical specimen that uses each coreceptor before and/or after initiating antiretroviral therapy.

The present invention yet further relates to a diagnostic method to monitor the suppression of CXCR4-specific strains in HIV-infected patients receiving antiretroviral therapy comprising determining the sequence of HIV envelope gene before and/or after initiating antiretroviral therapy.

Application of the diagnostic method further provides a way to monitor the effectiveness of antiretroviral therapy. Aspects of antiretroviral therapy that can be monitored, for example, are development of drug resistance and/or sensitivity. The diagnostic methods of the invention can be applied before initiating antiretroviral therapy to determine a suitable antiretroviral treatment regimen. The diagnostic methods of the claimed invention can also be applied after initiating antiretroviral therapy to monitor efficacy of a viral treatment regimen and where efficacy of the treatment is directly related to decrease of CXCR4 coreceptor use. The diagnostic methods of the invention can also be used to determine whether a putative antiretroviral therapy or treatment is efficacious in decreasing CXCR4 coreceptor use.

Antiretroviral therapy can include, but is not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including as examples regimens that have at least one protease inhibitor, or at least a reverse transcriptase inhibitor and a protease inhibitor; or at least two reverse transcriptase inhibitors with at least one protease inhibitor.

Typical reverse transcriptase inhibitors include nucleoside analogs, e.g., AZT (Zidovudine), ddi (didanosine), ddc (zalcitabine), D4T (stavudine), 3TC (lamivudine), Ziagen (abacavir), combivir (mix of AZT and 3TC), and non-nucleoside analogs, e.g., viramune (nevirapine), rescriptor (delavirdine), sustiva (efavirenz). Protease inhibitors include invirase (saquinavir), norvir (ritonavir), crixivan (indinavir), viracept (nelfinavir), agenerase (amprenivir), kaletra (lopinavir and ritonavir) and fortovase (saquinavir in a soft gelatin form). Thus, HAART can also be "triple cocktail" therapy—a three drug regimen to combat HIV wherein one of the three drugs is usually a protease inhibitor (and the other two are usually reverse transcritase inhibitors).

One skilled in the art (e.g. a physician, preferably specializing in the treatment of infectious disease) would use appropriate judgment and discretion in determining how often to apply the diagnostic methods to a test subject (e.g. a patient). Frequency of application can vary, depending on, for example, the age, sex, type of antiretroviral therapy administered to, or stage of disease progression in, a test subject.

One skilled in the art further understands the results of the diagnostic method to provide additional information about the stage of disease progression or therapeutic efficacy, depending on the amount of CXCR4 specific strain specificity of a test subject.

Application of the diagnostic methods to detect and/or monitor changes in coreceptor use is useful for assessing the effectiveness of antiretroviral therapy.

The present invention further relates to a composition that is a diagnostic composition which can be, for example in the form of a kit.

The diagnostic composition can comprise the components as defined herein above wherein said components are bound to/attached to and/or linked to a solid support. It is furthermore envisaged, that the diagnostic composition comprises nucleic acid sequences encoding a envelope protein, or a fragment thereof, preferably a V3 region fragment; or indicator cell lines of this invention; all of which can be contained on micro-chips identifiable with a suitable means for detection.

Solid supports are well known in the art and comprise, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. Suitable methods for fixing/immobilizing cells, nucleic acid sequences, or polypeptides of the invention are well known and include, but are not limited to ionic, hydrophobic, covalent interactions and the like.

The diagnostic composition of the present invention can be advantageously used as a kit, inter alia, for carrying out the method of the invention and could be employed in a variety of applications, e.g., as diagnostic kits, as research tools. Additionally, the kit of the invention can contain means for detection suitable for scientific, medical and/or diagnostic purposes. The manufacture of the kits follows preferably standard procedures that are known to the person skilled in the art. Kits can advantageously include instructions for use and/or admixture of ingredients.

In the present invention, it is additionally understood that HIV is a lentivirus, and the skilled artisan can readily understand that from the teachings herein, and the knowledge in the art, within the ambit of the invention are herein embodiments wherein the virus is a lentivirus other than HIV, including SIV and FIV, as in U.S. Pat. Nos. 5,863,542 and 5,766,598, and wherein the coreceptors are analogous (e.g. homologous) to CCR5 and CXCR4. As used herein, acquired immunodeficiency virus is interchangeable with HIV and encompasses other such viruses such as SIV and FIV. One skilled in the art can follow the teachings in the art to identify analogous coreceptors.

The present invention is additionally described by way of the following illustrative, non-limiting Examples, that provide a better understanding of the present invention and of its many advantages.

EXAMPLES

The Examples show that HAART not only reduces the quantity of virus but also affects HIV-1 coreceptor use. Briefly, methods were devised for quantifying the proportion of viruses in patient-derived virus that used each coreceptor and monitoring the effect of combination antiretroviral therapy, particularly HAART, on coreceptor use.

Example 1

Study Population

Coreceptor use was examined in twenty-two women who participated in two prospective studies of HIV-1 infection. Nineteen were enrolled in the Bronx-Manhattan site of Women's Interagency HIV Study (WIHS), a National Institutes of Health (NIH) multicenter study of the natural history of HIV-1 infection in women. Three took part in a study of HIV-1 pathogenesis performed at the Wadsworth Center of the New York State Department of Health in Albany, N.Y. Both studies included individuals with a broad spectrum of HIV-1 disease. The institutional review boards at each clinical site and the New York State Department of Health approved the investigation. Each woman provided informed consent at enrollment.

To examine the effect of combination antiretroviral therapy on HIV-1 coreceptor use, women infected with CXCR4 strains were sought. After screening twenty-two women, most with advanced HIV-1 disease, fifteen participants meeting the following criteria were studied: 1) viral isolates displayed CXCR4 zidovudine monotherapy strains while untreated or taking nucleoside analogues alone; and 2) antiretroviral therapy, when initiated, was documented by the WIHS database, Wadsworth study questionnaires, and records of treating physicians.

Sample Collection, Preparation, and Analysis

Once the study population was selected, blood was drawn and separated into plasma and cell components. Anastos et al. (2000) J. AIDS Hum. Retro. (in press); Fang et al. (1995). HIV-1 RNA in plasma was quantitated by using NucliSens (Organon Teknika Corp., Durham, N.C.), with a lower limit of quantitation of ~80 copies/ml. The CCR5 genotype of each patient was determined as described. Samson et al. (1996).

Derivation of Primary Viral Isolates and Biological Clones

Primary isolates of HIV-1 were obtained by co-culture with normal donor PBMCs. Fang et al. (1995). Viral isolates were titrated in PBMCs. Fang et al. (1995). Biological clones were derived from primary isolates by short-term limiting dilution cloning. Connor et al. (1997).

Patient Population and Response to Therapy

Initially, most of the fifteen women displayed high plasma HIV-1 RNA levels and CD4+ cell depletion (means of 5.22 $\log_{10}$ copies/ml and 147 cells/mm$^3$, respectively). At that time, eight women were receiving antiretroviral therapy, primarily zidovudine monotherapy. While under study, however, 12 initiated new combination regimens; 9 received HAART (Group I) and 3 received two or more nucleoside analogues (Group II). Three individuals, by contrast, did not initiate new therapy during the study (Group III) (Table 1). In Table 1, "Before therapy" refers to data obtained at the visit immediately preceding initiation of new two or three drug antiretroviral therapy in Groups I & II. For Group III, data from the first time point are shown (a). "Follow-up" refers to data obtained at the first time point following the initiation of the anti-HIV therapy listed for Groups I & II. For Group III, data from the final time point are displayed (b). Comparisons of λ before and after initiation of new, combination antiretroviral therapy were statistically significant for Group I, HAART recipients (c), (P=0.023) and Groups I & II combined, consisting of all treated patients (P=0.003).

TABLE 1

Patient Characteristics Before and After Antiretroviral Therapy

| | Status Before Combination Therapy[a] | | | | Follow-up Status[b] | | | |
|---|---|---|---|---|---|---|---|---|
| Pt. | HIV-1 RNA, log copies per ml | CD4+ count, cells per mm3 | Anti-HIV Therapy | Λ, proportion of HIV-1 Using R5 | HIV-1 RNA, log copies per ml | CD4+ count, cells per mm3 | Anti-HIV Therapy | λ, proportion of HIV-1 Using R5 |
| | | | | Group I: HAART Recipients | | | | |
| 1 | 5.30 | 188 | AZT | 0.36 | 5.08 | 578 | 3TC, d4T, Nel | 1.00 |
| 2 | 5.69 | 3 | None | 0.00 | 3.41 | 90 | 3TC, d4T, Nel | 1.00 |
| 3 | 5.75 | 291 | None | 0.34 | 4.54 | 370 | AZT, 3TC, Saq | 0.45 |
| 4 | 5.28 | 9 | d4T | 0.36 | 3.08 | 15 | 3TC, d4T, Rit | 0.36 |
| 5 | 6.08 | 41 | None | 0.36 | 4.96 | 11 | 3TC, d4T, Saq | 0.90 |
| 6 | 5.11 | 19 | None | 0.45 | 3.70 | 24 | 3TC, d4T, Ind | 1.00 |
| 7 | 4.94 | 42 | AZT | 0.36 | 5.61 | 10 | 3TC, d4T, Ind | 0.36 |
| 8 | 5.65 | 0 | AZT, ddI | 0.44 | 5.29 | 23 | 3TC, d4T, Ind | 1.00 |

TABLE 1-continued

Patient Characteristics Before and After Antiretroviral Therapy

| | Status Before Combination Therapy[a] | | | | Follow-up Status[b] | | | |
|---|---|---|---|---|---|---|---|---|
| Pt. | HIV-1 RNA, log copies per ml | CD4+ count, cells per mm3 | Anti-HIV Therapy | Λ, proportion of HIV-1 Using R5 | HIV-1 RNA, log copies per ml | CD4+ count, cells per mm3 | Anti-HIV Therapy | λ, proportion of HIV-1 Using R5 |
| 9 | 5.58 | 259 | AZT | 0.90 | 4.86 | 282 | 3TC, d4T, Ind | 1.00 |
| Group II: Recipients of Combination Antiretroviral Therapy | | | | | | | | |
| 10 | 5.04 | 307 | AZT | 0.00 | 4.58 | 378 | 3TC, ddI | 1.00 |
| 11 | 5.10 | 222 | AZT, ddI | 0.00 | 4.94 | 213 | AZT, 3TC, d4T | 0.36 |
| 12 | 5.04 | 251 | None | 0.36 | 4.23 | 345 | AZT, 3TC | 1.00 |
| Group III: Recipients of No Therapy or AZT Monotherapy | | | | | | | | |
| 13 | 4.32 | 191 | None | 0.45 | 4.13 | 184 | None | 0.36 |
| 14 | 4.28 | 670 | None | 0.52 | 3.83 | 429 | None | 0.36 |
| 15 | 5.23 | 43 | AZT | 0.00 | 5.36 | NA | None | 0.00 |
| Mean Values for Treatment Groups | | | | | | | | |
| Group I | 5.49 | 94 | | 0.40 | 4.50 | 155 | | 0.74[c] |
| Group II | 5.06 | 260 | | 0.12 | 4.58 | 312 | | 0.79 |
| Group I & II, Combined | 5.38 | 136 | | 0.33 | 4.52 | 194 | | 0.75[c] |
| Group III | 4.61 | 301 | | 0.32 | 4.44 | 307 | | 0.24 |

For those initiating new therapy, HIV-1 RNA levels dropped by an average of 0.86 $\log_{10}$ copies/ml and CD4+ counts increased by an average of 58 cells/ml by the first study visit after starting the new regimens. The viral levels rebounded by 0.69 $\log_{10}$ copies/ml, however, by the end of the 28.5 month mean follow-up period for treated patients, at which time 11 of the 12 women continued to take antiretroviral therapy (6 HAART, 5 two drug regimens).

Assay for Coreceptor Use

Changes in coreceptor use of primary HIV-1 isolates and biological clones from participants in the study were followed by using a HOS-CD4+ cell system. The parental HOS-CD4+ line is a human osteogenic sarcoma cell line stably expressing high levels of CD4. HOS-CD4+ cells transfected with genes encoding either CCR5 or CXCR4 in addition to CD4 (cell lines HOS-CD4.CCR5 and HOS-CD4.CXCR4 respectively) served as indicator lines for coreceptor use. Deng et al. (1996). To determine coreceptor use, HOS-CD4.CCR5 and HOS-CD4.CXCR4 cells were seeded onto 12-well plates and, after 24 hours, inoculated with a standard quantity of titered virus; $10^2$ TCID$_{50}$ of first passage primary viral isolates or biological clones were assayed in duplicate. HIV JR-FL, and LAV/HTLV-IIIB inoculated in parallel as CCR5- and CXCR4-specific positive control viruses, respectively, and uninoculated cells were used as negative controls. To eliminate any artifacts resulting from infection via low levels of endogenous coreceptor expression, parental HOS-CD4+ cells were also inoculated with duplicate primary and control isolates.

Supernatants were harvested at day 10 after infection and analyzed for HIV-1 p24 antigen using a commercially available ELISA assay (NEN Life Science Products, Boston). ELISA values were standardized so that 0 pg/ml was set at the level equal to three times the mean value of the negative controls. A culture was considered positive if the p24 antigen level was equal to or greater than 25 pg/ml. Experimental results were discarded if: 1) any parental HOS-CD4+ culture tested positive; or 2) any JR-FL or LAV/HTLV-IIIB positive control culture tested negative. If the variance in p24 antigen level between duplicate cultures was greater than 25%, the coreceptor use assay for that particular viral isolate was repeated. Results of the coreceptor use assay were then categorized in a semiquantitative manner according to p24 antigen level as follows: negative (p24<25 pg/ml), +/−(25-50 pg/ml), 1+(50-250 pg/ml), 2+(250-500 pg/ml), and 3+($\geq$500 pg/ml).

Phenotypic Characterization

The presence of syncytium-inducing (SI) variants of HIV-1 in patient primary viral isolates was determined by infection of MT-2 cell cultures as previously described. Koot et al. (1993). A pooled stock of HIV LAV/HTLVIII was used as a positive control.

Example 2

Antiretroviral Therapy Preferentially Suppresses CXCR4 Strains

Fourteen women initially displayed viral populations composed of both CCR5 and CXCR4 viruses (FIG. 1) and one displayed virus that exclusively used CXCR4. CXCR4 viruses persisted at subsequent time points in patients who did not initiate new combination therapy, a finding exemplified in FIG. 1 by Patient 13, who remained untreated throughout the study, and Patients 1, 2, and 8, whose virus was sampled on multiple occasions before new therapy commenced. Viruses using CXCR4 appeared to be preferentially suppressed, however, when new regimens were initiated. Not only were CXCR4 strains eliminated by the first time point after starting new therapy in half of the treated women (FIG. 1., Patients 1, 2, 6, 8, and 10), but the proportion of these viruses seemed to be diminished in most of the others. In addition, patients who experienced a rebound in HIV-1 RNA levels and CXCR4 strains while on therapy often achieved suppression of CXCR4 strains a second time when the antiretroviral regimen was changed (FIG. 1., Patients 2 and 8).

Coreceptor Use by Biologically Cloned Viruses

Delineation of the proportion of individual viruses using each coreceptor was prompted by two aspects of the pattern of HIV-1 coreceptor use in these individuals. First, analyses of primary viral isolates by the HOS-CD4+ system indicated coreceptor use by both CCR5 and CXCR4 viruses at many time points (FIG. 1). Because primary isolates comprise a molecular mixture of viral quasispecies, we wished to determine whether use of both coreceptors was due to dual tropic viruses or a mixture of individual viruses with CCR5 and CXCR4 tropisms. In addition, to compare coreceptor use rigorously over time, it is desirable to quantitate the proportion of virus using each coreceptor. For these reasons, biologic clones, which were derived from the patients' primary isolates by performing limiting dilution cultures were isolated. Coreceptor use was then determined for 25 clones from each isolate by employing the HOS-CD4+ cell system. Biologic clones from these patients used either CCR5 or CXCR4; no dual tropic viruses were detected among the 525 clones by using our assay system. In addition, the distribution of coreceptor use by the clones generally confirmed the semiquantitative results obtained for primary isolates; proportions of HIV-1 using each coreceptor appeared roughly similar whether the cloned virus or primary isolates were examined (Table 2A, HIV-1 coreceptor use in primary viral isolates and biologic clones).

TABLE 2A

| Pt | Months After Baseline | Treatment | Co-Receptor Use of Primary Viral Isolates | | Distribution of Co-Receptor Use by Biologic Clones | |
|---|---|---|---|---|---|---|
| | | | CCR5 | CXCR4 | CCR5 | CXCR4 |
| 2 | 16 | AZT, 3TC | +++ | +++ | 8 | 17 |
|   | 18 | HAART | + | − | 25 | 0 |
|   | 26 | HAART | + | +++ | 4 | 21 |
| 5 | 0 | None | ++ | +++ | 11 | 14 |
|   | 6 | HAART | +++ | + | 21 | 4 |
|   | 9 | d4T, Ind | +++ | +++ | 10 | 15 |
|   | 16 | HAART | +++ | − | 25 | 0 |
| 14 | 0 | None | +++ | ++ | 13 | 12 |
|    | 7 | None | +++ | +++ | 9 | 16 |

In Table 2A coreceptor use was determined for the primary viral isolate obtained at each time point and for 25 biologic clones derived from each isolate.

Studies of biologic clones obtained at serial time points also confirmed that the predominant viral population shifted from CXCR4 to the less pathogenic CCR5 after initiation of new combination antiretroviral therapy (Table 2A). For example, analyses of virus obtained from Patient 2 sixteen months after baseline and eight months after initiation of double therapy showed only eight clones that used CCR5 as compared to seventeen that used CXCR4. After a switch to a HAART regime that included two new drugs, however, the viral population in this patient shifted and all 25 biologic clones used CCR5. A similar pattern was exhibited by biologic clones from Patient 5, whose virus shifted dramatically to CCR5 on the two occasions that HAART was initiated. Patient 14, by contrast, remained untreated and her viral population evolved to comprise a larger proportion of clones using CXCR4 over time.

The MT2 assay to detect SI viruses in culture was also performed on primary isolates derived at each time point. These results confirmed the pattern of HIV-1 coreceptor use described here. Thirteen of the fifteen patients were infected initially with SI virus. In all eleven of those who displayed SI virus and received new combination therapy, the phenotype changed at least transiently to non-syncytia inducing (NSI) after treatment (data not shown).

Sequence Analyses of the HIV-1 V3 Loop

HIV-1 virions were isolated from plasma samples as described. Fang et al. (1996) J. AIDS Hum. Retro. 12:352-7. Reverse transcriptase polymerase chain reaction amplification produced a 920-bp amplicon spanning the V3 region of the env gene. Reaction conditions were controlled rigorously to minimize recombination and other artifacts. Fang et al. (1996). Amplified products were cloned into a TOPO™ TA vector (Invitrogen, Carlsbad, Calif.), verified by restriction digestion, and sequenced. Alignment of the sequences was initially done using the PILEUP program in the GCG Suite (Genetics Computer Group, Madison, Wis.), then checked manually. Envelope sequences were used to predict coreceptor use on the basis of the overall charge of the V3 loop and the presence of basic or acidic residues at positions 275 and 287 of the env gene. Bhattacharyya et al. (1996); and Hung et al. (1999).

Coreceptor Use Determined by Sequence Analysis of HIV-1 RNA Molecular Clones

These sequences predicted a pattern of coreceptor use that essentially paralleled the one obtained by using viral culture (Table 2B, Coreceptor use determined by cocultivation of PBMCs vs. sequence analysis of plasma HIV-1 RNA). Table 2B shows a comparison of coreceptor use over time determined by two methods in representative study patients. At each time point, coreceptor use was assayed by co-cultivating PBMCs and determining the V3 loop sequence of virion-derived HIV-1 RNA.

The sequence data underscored the change in coreceptor use seen after initiation of treatment. These experiments suggest that study of cultivated virus reflects the coreceptor use of currently replicating virus and is likely to reveal the shifts in viral populations that occur as a result of recent antiretroviral therapy.

TABLE 2B

| Pt | Months After Baseline | Treatment | Co-Receptor Use by Cocultivated Virus | | Distribution of Co-Receptor Use Predicted by V3 Loop Sequences | | Total # of Clones |
|---|---|---|---|---|---|---|---|
| | | | CCR5 | CXCR4 | CCR5 | CXCR4 | |
| 1 | 6 | AZT | +++ | +++ | 9 | 4 | 13 |
|   | 33 | HAART | +++ | − | 13 | 0 | 13 |
|   | 36 | HAART | +++ | + | 8 | 2 | 10 |
| 2 | 16 | AZT, 3TC | +++ | +++ | 1 | 13 | 14 |
|   | 22 | HAART | + | ++ | 0 | 13 | 13 |
|   | 26 | HAART | + | +++ | 3 | 8 | 11 |
| 5 | 0 | None | ++ | +++ | 2 | 10 | 12 |
|   | 6 | HAART | +++ | + | 8 | 3 | 11 |
|   | 9 | d4T, Ind | +++ | +++ | 2 | 10 | 12 |
|   | 16 | HAART | +++ | − | 12 | 0 | 12 |
| 14 | 0 | None | +++ | ++ | 5 | 6 | 11 |

Statistical Methods

The Wilcoxon Rank Sum Test was used to make comparisons between the magnitude of log viral level, CD4+ counts, and $\lambda$ values. Data for factors relating to changes in $\lambda$ values were analyzed by multivariate Poisson regression. Variables included log HIV-1 RNA levels, changes in viral levels, CD4+ cell counts, changes in CD4+ cell counts, and indicator variables for levels of antiretroviral therapy.

To quantitate HIV-1 coreceptor use, we constructed a variable, λ, as the proportion of strains using CCR5. Lambda=1 represents an isolate in which all strains prefer the CCR5 coreceptor but λ=0 indicates that all prefer CXCR4. Lambda values were assessed by utilizing qualitative assay data derived from primary isolates, biologic clones, and sequences of the V3 portion of the env gene. In determination of the coreceptor use of 525 biologic clones, none was dual tropic, suggesting that true dual tropic viruses are rare when using our assay method. It was therefore assumed for this calculation that the probability of a single virion possessing the phenotypic attributes of both coreceptors is small. Thus, for the vast majority of virions, each virion uses either CCR5 or CXCR4. This relationship can be stated as a mixture $D=\lambda(CCR5)+(1-\lambda)(CXCR4); 0 \leq \lambda \leq 1$, where D is the distribution of viral phenotypes. By design, it is a binomial population.

Lambda values were constructed by relating data derived from the same patient sample by using three different analyses: biologic cloning, V3 sequencing of patient-derived molecular clones, and qualitative assays of primary isolates. To construct λ values, we first calculated the proportion of biologic and, if available, molecular clones using CCR5 at each time point, then linked the proportion to the qualitative coreceptor use score (− to 3+) of primary isolates obtained simultaneously. Data that were not available were interpolated. The data were transformed to approximate a Poisson distribution. Poisson regression analysis was then performed to determine the factors associated with changes in λ values.

Quantitation of Coreceptor Use by CCR5 and CXCR4

The large number of biologic and molecular clones permitted derivation of a system to quantitate the proportion of virus in a clinical specimen that uses each coreceptor. In this system, lambda (λ) is a continuous, nonlinear variable between one and zero derived from the results presented here showing coreceptor use by biologically and molecularly cloned virus; it describes the mixed proportion of viruses using CCR5 and CXCR4. A λ value near one describes a population of viruses that almost all use CCR5; a value near zero describes a population that almost all use CXCR4. By applying this method, it was determined that the proportion of virus using each coreceptor for each patient over time.

To quantitate the effect of combination therapy on HIV-1 coreceptor use, we compared the λ values of virus obtained at the visits before and immediately after initiating new combination therapy. This comparison demonstrated a clear, statistically significant shift of the predominant viral population from CXCR4 to CCR5 (Table 1). The mean λ values for virus from all twelve patients starting combination therapy (Groups I & II) changed from 0.33 to 0.75 (P=0.003 by using the binomial proportion comparison test). For the subset of nine who initiated HAART (Group I), the shift in λ extended from 0.40 to 0.74 (P=0.023). In addition, we assessed separately the effect of initiating treatment with two or more nucleoside analogues and no protease inhibitor on coreceptor use. Five of the patients who ultimately received HAART had received regimens consisting of two nucleoside analogues previously. The λ values of virus obtained before or after initiation of two or more nucleoside analogues in a group of eight patients (Group II and Patients 1, 2, 6, 7, and 9) were compared; in this group the λ values changed from 0.30 to 0.84 (P=0.008). By contrast, in the Group III patients, who did not initiate combination therapy, the mean λ value decreased from 0.32 to 0.24 during the course of this study. These numerical comparisons of coreceptor use demonstrated a shift in the predominant viral population from CXCR4 to CCR5 following initiation of a variety of combination antiretroviral regimens.

Long-term Analysis of Antiretroviral Therapy, Viral Level, and CD4+ Cell Count Effects on Coreceptor Use The period of follow-up for treated women in this study averaged 28.5 months, during which their coreceptor use, plasma HIV-1 RNA levels, and CD4+ cell count varied, sometimes in concert (FIG. 1). The multivariate regression indicated that antiretroviral therapy with two or more drugs was by far the most significant factor in determining λ, the numerical expression of the proportion of viruses using CCR5 (P=0.01). Although changes in viral level and CD4+ cell count had a significant effect on λ in univariate analysis, they lost all significance when considered in a multivariate regression analysis with antiretroviral therapy. The strength of the relationship between initiation of therapy and shift in HIV-1 coreceptor use is reflected in the course of treated individuals like Patient 8, who maintained high plasma HIV-1 RNA levels during treatment but demonstrated a substantial, long-term shift in viral population toward CCR5 (FIG. 1).

Example 3

Dynamics of HIV-1 Coreceptor Utilization Switch

Figure 2:
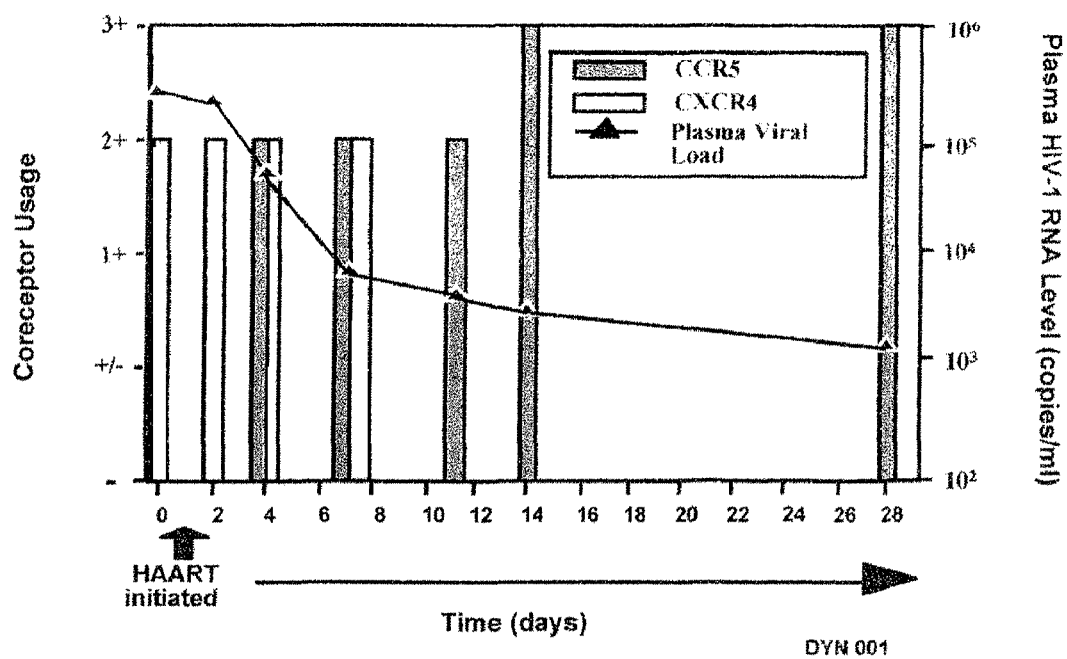

The dynamics of the shift in coreceptor utilization immediately following initiation of HAART have been characterized. Coreceptor utilization immediately following the initiation of HAART was determined by studying virus derived from the patient's PBMC's. Results show the following: 1) this patient was unusual in that her initial viral population was composed of X4 viruses only, 2) by the third day after the initiation of HAART, the viral population had switched to equal proportions of X4 and R5 using strains, and 3) by day 11, the population had entirely switched to R5 using virus (FIG. 2).

Comparison of coreceptor usage in this patient was also performed using a recombinant assay that does not require culturable primary isolates. The results of the recombinant assay were identical to the results obtained using virus derived from the patient's PBMC's. These data document a rapid, complete switch in coreceptor utilization by virus in peripheral blood that occurred less than two weeks after initiating HAART. To understand the complexities of HIV-1 pathogenesis, it is necessary to consider the heterogeneity of viral populations and viral reservoirs. This approach will provide insight into the dynamics of suppressing different populations of virus.

Example 4

Rapid Cell Fusion Assay for Coreceptor Utilization

Viral coreceptor usage was separately evaluated through the use of a Rapid Cell Fusion Assay. This assay enables determination of coreceptor usage from cloned HIV env gene sequences obtained directly from patient samples (e.g. blood, mucosal tissue). This method allows for greater efficiency in determination of viral coreceptor usage, by circumventing the need for cultivation of primary isolates. The Rapid Cell Fusion Assay can advantageously produce a result within one week after obtaining a patient sample. In addition, the Rapid Cell Fusion Assay allows study of patient-derived virus obtained from sites other than the peripheral blood, particularly those sites from which cultured virus cannot be obtained. For example, while circulating macrophages and $CD4^+$ T cells are the dominant reservoir of HIV-1, viral populations distinct from those in the peripheral blood exist in many tissue reservoirs, including the genital mucosa. It is important to study these different reservoirs as HIV-1 viral populations in infected individuals demonstrate marked heterogeneity, with virus varying in the same compartment over time and in different compartments contemporaneously. Myers et al. (1995); Meyerhans et al. (1989); Vernazza et al. (1994); Cheng-Mayer et al. (1989); Koyanagi et al. (1987). Even in patients receiving combination anti-HIV-1 therapy, studies of lymphoid tissue reservoirs showed persistent viral replication in lymph nodes, with viral load in tissue exceeding that in plasma by orders of magnitude in most cases. Wong et al. (1997); Cavert et al. (1997); Haase et al. (1996).

Steps of the Rapid Cell Fusion Assay

The HL3T1 cell line was derived by stable transfection of parental HeLa cells with a chloramphenicol acetyltransferse (CAT) reporter construct containing a CAT gene is linked to an HIV-1 LTR promoter. The HL3T1 cells produce CAT protein only upon introduction of an active HIV-1 Tat protein. HL3T1 cells were transfected with a cloned HIV env gene derived from a patient of interest. The cloned env gene product is expressed on the surface of the HL3T1 cells.

Indicator cell lines GHOST.CCR5 and GHOST.CXCR4 (respectively hereinafter "R5-tat" and "X4-tat") cells were transfected with pSV2tat72, a construct expressing high levels of HIV-1 Tat under the control of the SV40 early promoter.

HL3T1 cells containing a cloned patient HIV env gene were fused to R5-tat and X4-tat cells. Cell surface envelope protein variants will selectively interact with either CCR5 or CXCR4. Fusion only occurs when an HL3T1 envelope protein interacts with an indicator cell expressing a compatible coreceptor. Therefore, HL3T1 cells will fuse with either R5-tat and X4-tat, depending on the patient's HIV env gene specificity. To initiate fusion, transfected HL3T1 and R5-tat or X4-tat cells were mixed in 6-well plates at 37° C. and allowed to fuse for 48 hours. To quantitate fusion, the cells were lysed with 0.5% NP-40. Fusion of HL3T1 cells to R5-tat or X4-tat activated CAT gene expression. Aliquots of the cell lysates were monitored for CAT production using a commercially available kit (CAT-ELISA, Boehringer Mannheim).

Twenty-five clones from each sample were analyzed to ensure that the fusion assay reflected the heterogeneous nature of HIV-1 populations. Sample results of the Rapid Cell Fusion Assay for Coreceptor Utilization are presented below. For all env clones assayed in this manner, sequence analysis has revealed a 97% correlation between coreceptor usage and predicted env genotype.

| CLONE | V3 LOOP SEQUENCE | CORECEPTOR | |
|---|---|---|---|
| AF2P12-1 | CIRPNNNTRTSIRIGPGQAFYATGNIIGDIRQAYC | CCR5 | (SEQ ID NO. 1) |
| AF2P12-2 | CIRPNNNTRTSIRIGPGQAFYATGNIIGGIRQAYC | CCR5 | (SEQ ID NO. 26) |
| AF2P12-3 | CIRPNNNTRTSIRIGPGQAFYATGNIIGDIRQAYC | CCR5 | (SEQ ID NO. 1) |
| AF2P12-4 | CIRPNNNTRTSIRIGPGQAFYATGNIIGDIRQAYC | CCR5 | (SEQ ID NO. 1) |
| AF2P12-6 | CIRPNNNTRTSIRIGPGQAFYATGNIIGDIRQAYC | CCR5 | (SEQ ID NO. 1) |
| AF2P12-8 | CIRPNNNTRTSIRIGPGQAFYATGNIIGDIRQAYC | CCR5 | (SEQ ID NO. 1) |
| AF2P12-9 | CIRPNNNTRTSIRIGPGQAFYATGNIIGDIRQAYC | CCR5 | (SEQ ID NO. 1) |
| AF2P12-10 | CIRPNNNTRTSIRIGPRQAFYATGNIIGDIRQAYC | CXCR4 | (SEQ ID NO. 2) |
| AF2P12-11 | CIRPNNNTRTSIRIGPGQAFYATGNIVGDIRQAYC | CCR5 | (SEQ ID NO. 3) |
| AF2P12-12 | CIRPNNNTRTSIRIGPGQAFYATGNIIGDIRQAYC | CCR5 | (SEQ ID NO. 1) |
| AF3P-2 | ........RKSVHIGPGQAFYATGDIIGNIRKAHC | negative | (SEQ ID NO. 4) |
| AF3P-4 | CTRPNNNTRKSVHIGPGQAFYATGDIIGNIRKAHC | CCR5 | (SEQ ID NO. 5) |
| AF3P-5 | CTRPNNNTRKSVHIGPGQAFYATGDIIGNIRKAHC | CCR5 | (SEQ ID NO. 5) |
| AF3P-6 | CTRPNNNTRKSVHIGPGQAFYATGDIIGNIRQAHC | CCR5 | (SEQ ID NO. 6) |
| AF3P-7 | CTRPNNNTRKSVHIGPGQAFYATGDIIGNIRKAHC | CCR5 | (SEQ ID NO. 5) |
| AF3P-8 | CTRPNNNTRKSVHIGPGQAFYATGDIIGNIRKAHC | CCR5 | (SEQ ID NO. 5) |
| AF3P-9 | CTRPNNNTRKSVHIGLGQAFYATGDIIGNIRKAHC | CCR5 | (SEQ ID NO. 27) |
| AF3P-10 | CTRPNNNTRKSVHIGPGQAFYATGDIIGNIRKAHC | CCR5 | (SEQ ID NO. 5) |
| AF3P-11 | CTRPNNNTRKSVHIGPGQAFYATGDILGNIRQAHC | CCR5 | (SEQ ID NO. 28) |
| AF3P-12 | CTRPNNNTRKSVHIGPGQAFYATGDIIGNMRKAHC | CCR5 | (SEQ ID NO. 7) |
| AF5P-5 | CTRPNNNTRKSVHIGPGQAFYATGDIIGDIRQAYC | CCR5 | (SEQ ID NO. 29) |
| AF5P-6 | CTRPNNNTKKSVHIGPGQAFYATGDIIGDIRQAYC | CCR5 | (SEQ ID NO. 30) |
| AF5P-8 | CTRPNNNTRKSVHIGPGQAFYATGDIIGDIRQAYC | CCR5 | (SEQ ID NO. 29) |
| AF6P-1 | CTRPINNRRKSIHMGPGQAFYGT.DDIIGDIRKARC | CCR5 | (SEQ ID NO. 8) |

-continued

| CLONE | V3 LOOP SEQUENCE | CORECEPTOR | |
|---|---|---|---|
| AF6P-3 | CTRPINNRRKSIHMGPGQAFYGT.DDIIGDIRKARC | CCR5 | (SEQ ID NO. 8) |
| AF6P-7 | CTRPSNNRRKSIHKGDQDKHSMEHDDVIGDIRKARC | negative | (SEQ ID NO. 9) |
| AF6P-9 | CTRPINNRRKSIHMGPGQAFYGT.DDIIGDIRKARC | CCR5 | (SEQ ID NO. 8) |
| AF6P-10 | CTRPINNRRKSIHIGPGQAFYGT.DDIIGDIRQAHC | CCR5 | (SEQ ID NO. 32) |
| AF6P-11 | CTRPSNNRRKSIHMGPGQAFYGT.DDIIGGIRKARC | CCR5 | (SEQ ID NO. 33) |
| AF6P-12 | CTRPSNNRRKSIHMGPGQAFYGT.DDIIGDIRKARC | CCR5 | (SEQ ID NO. 34) |
| AF7P-9 | CIRPNNNTRQSVHIGPGQALYTTEIIGDIRKAHC | CCR5 | (SEQ ID NO. 11) |
| AF7P-12 | CIRPNNNTRQSVHIGPGQALYTTEIIGDIRKAHC | CCR5 | (SEQ ID NO. 11) |
| AF9P2-3 | CTRPNNNTITSIRIGPGQAFYATGSIIGNIRQAHC | CCR5 | (SEQ ID NO. 12) |
| AF9P2-4 | CTRPNNNTITSIRIGPGQAFYATGSIIGNTRQAHC | CCR5 | (SEQ ID NO. 13) |
| AP9P2-7 | CTRPNNNTITSIRIGPGQAFYATGSIIGNIRQAHC | CCR5 | (SEQ ID NO. 12) |
| AF9P2-9 | CTRPNNNTITSIRIGPGQAFYATGSIIGNIRQAHC | CCR5 | (SEQ ID NO. 12) |
| AF9P2-10 | CTRPNNNTITSIRIGPGQAFYATGSIIGNIRQAHC | CCR5 | (SEQ ID NO. 12) |
| AF9P2-11 | CTRPNNNTITSIRIGPGQAFYATGSIIGNIRQAHC | CCR5 | (SEQ ID NO. 12) |
| AF9P2-12 | CTRPNNNTITSIRIGPGQAFYATGSIIGNIRQAHC | CCR5 | (SEQ ID NO. 12) |
| AF10P97-2 | CTRPNDNIRKSVHIGPGQAFYATGDIIGDIRRAHC | CCR5 | (SEQ ID NO. 14) |
| AF10P97-4 | CTRPNDNIRKRVHIGPGQAFYATGDVIGDIRRAHC | CXCR4 | (SEQ ID NO. 31) |
| AF10P97-6 | CTRPNDNIRKSVHIGPGQAFYATGDIIGDIRRAHC | CCR5 | (SEQ ID NO. 14) |
| AF10P97-11 | CTRPNDNIRKSVHIGPGQAFYATGDIIGDIRRAHC | CCR5 | (SEQ ID NO. 14) |

Sequence Identifiers
(SEQ ID NO: 1)  CIRPNNNTRTSIRIGPGQAFYATGNIIGDIRQAYC
(SEQ ID NO: 2)  CIRPNNNTRTSIRIGPRQAFYATGNIIGDIRQAYC
(SEQ ID NO: 3)  CIRPNNNTRTSIRIGPGQAFYATGNIVGDIRQAYC
(SEQ ID NO: 4)  RKSVHIGPGQAFYATGDIIGNIRKAHC
(SEQ ID NO: 5)  CTRPNNNTRKSVHIGPGQAFYATGDIIGNIRKAHC
(SEQ ID NO: 6)  CTRPNNNTRKSVHIGPGQAFYATGDIIGNIRQAHC
(SEQ ID NO: 7)  CTRPNNNTRKSVHIGPGQAFYATGDIIGNMRKAHC
(SEQ ID NO: 8)  CTRPTNNRRKSIHMGPGQAFYGT.DDIIGDIRKARC
(SEQ ID NO: 9)  CTRPSNNRRKSIHKGDQDKHSMEHDDVIGDIRKARC
(SEQ ID NO: 10) CTRPINNRRKSIHIGPGQAFYGT.DDIIGDIRQAHC
(SEQ ID NO: 11) CIRPNNNTRQSVHIGPGQALYTTEIIGDIRKAHC
(SEQ ID NO: 12) CTRPNNNTITSIRIGPGQAFYATGSIIGNIRQAHC
(SEQ ID NO: 13) CTRPNNNTITSIRIGPGQAFYATGSIIGNTRQAHC
(SEQ ID NO: 14) CTRPNDNIRKSVHIGPGQAFYATGDIIGDIRRAHC Methods of env Gene Cloning In cloning the env gene from patients by the use of long RT-PCR, two potential problems may result: 1) recombination between molecules; and 2) underestimates of sequence diversity. High fidelity cloning of the samples above was achieved by routine performance of multiple RT reactions on limiting dilutions of RNA, followed by multiple PCR's on cDNAs obtained from each RT reaction. Performance of multiple PCR's on each cDNA preparation increased the likelihood of amplifying a different HIV-1 RNA species. These measures also decrease the chance of recombination. Accordingly, the following protocol was developed:

1. Peripheral blood was collected and separate into plasma and cell components. Other fluids and tissues derived from an HIV-infected individual can also be used, with minor modifications to the RNA extraction protocol outlined below.

2. HIV-1 RNA was quantitated in plasma by using NucliSens (Organon Teknika Corp., Durham, N.C.), with a lower limit of quantitation set at approximately 80 copies/ml.

3. RNA extraction:
   a) HIV-1 RNA was extracted from plasma using Qiagen's Viral RNA Kit and following the manufacturer's standard protocol.
   b) Samples were standardized by extracting a volume of plasma equal to 10000 copies of HIV-1 RNA. For example, if the patient's plasma viral load is 25000 copies/ml, 0.4 ml of plasma in the extraction should be used.
   c) Following extraction, the virus was resuspended in 100 ul of Rnase-free water (to give a final concentration of ≦100 copies of HIV-1 RNA per ul) and optionally treated with Rnase-free Dnase to remove any contaminating DNA.

Figure 3:
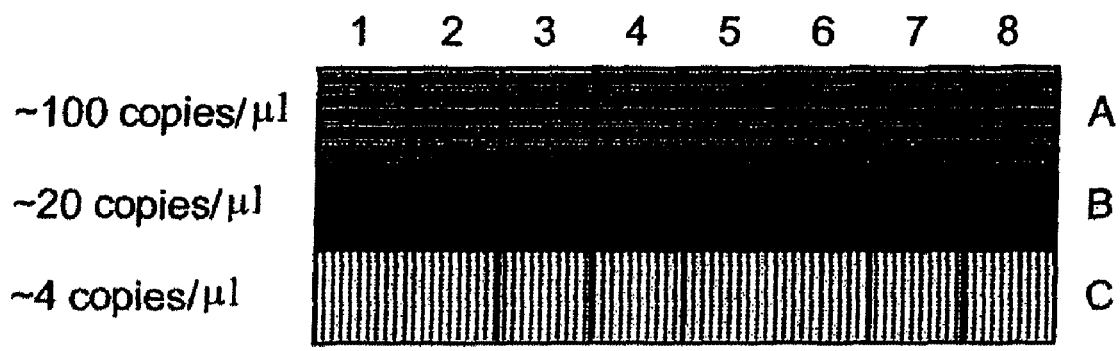

4. RT-PCR using limiting dilution to ensure minority species amplification:
   a) Samples of serially diluted RNA template were generated in a series of 1:5 dilutions using the following template concentrations:
      ~100 copies/μl
      ~20 copies/μl
      ~4 copies/μl
      This dilution series is sufficient to ensure minority species amplification. Conditions are adaptable to achieve limiting dilutions.
   b) 1 ul aliquots of RNA template were distributed into the wells of a PE2400 or PE9700 PCR thermocycler tray-retainer and 8-24 tubes containing of each RNA dilution were prepared. An example of the template set-up for a PE2400 is shown in FIG. 3.
   c) An RT reaction mix was prepared:

| reagent | per reaction |
| --- | --- |
| Rnase-free H$_2$O | 2 ul |
| 10x PCRII buffer | 2 ul |
| 25 mM MgCl$_2$ | 4 ul |
| 10 mM dATP | 2 ul |
| 10 mM dCTP | 2 ul |
| 10 mM dGTP | 2 ul |
| 10 mM dTTP | 2 ul |
| Rnase Inhibitor | 1 ul |
| 50 mM Random Hexamers | 1 ul |
| MMLV RT (50 U/ul) | 1 ul |

All reagents are commercially available from Perkin Elmer. Each well received a 19 ul aliquot. Samples were incubated for 60 minutes at 37° C., followed by heat inactivation for 5 minutes at 95° C. Samples were stored at 4° C.

d) The Primary PCR reaction mix was prepared:

| reagent | per reaction |
| --- | --- |
| sterile H$_2$O | 67.5 ul |
| 10x PCRII buffer | 8 ul |
| 25 mM MgCl$_2$ | 2 ul |
| primer HIVGao1F (20 uM) | 1 ul |
| primer HIVGao1R (20 uM) | 1 ul |
| Taq polymerase (50 U/ul) | 0.5 ul |

Primer sequences for HIVGao1F and HIVGao1R were:

```
                                          (SEQ ID NO: 15)
HIVGao1F: 5'-GGCTTAGGCATCTCCTATGGCAGGAAGAA-3'

(SEQ ID NO: 16)
HIVGao1R: 5'-GGCTTAGGCATCTCCTATGGCAGGAAGAA-3'
```

80 ul aliquots were transferred into each well containing the RT mix. The cycle parameters were:

| Cycle file | Temp. | Time |
| --- | --- | --- |
| 1 hold: | 94° C. | 5 minutes |
| 5 cycles: | 94° C. | 1 minute |
|  | 50° C. | 1 minute |
|  | 72° C. | 3.5 minute |
| 30 cycles: | 94° C. | 1 minute |
|  | 55° C. | 1 minute |
|  | 72° C. | 3.5 minute |
| 1 hold: | 72° C. | 10 minutes |
| 1 hold: | 4° C. | until ready for nested reaction | e) A nested PCR reaction mix was prepared:

| reagent | per reaction |
| --- | --- |
| sterile H$_2$O | 75.5 ul |
| 10x PCRII buffer | 10 ul |
| 25 mM MgCl$_2$ | 6 ul |
| 10 mM dNTP blend | 4 ul |
| primer HIVGao2F (20 uM) | 1 ul |
| primer HIVGao2R (20 uM) | 1 ul |
| Taq polymerase (50 U/ul) | 0.5 ul |

Primer sequences for HIVGao2F and HIVGao2R are:

```
                                          (SEQ ID NO: 17)
HIVGao2F: 5'-AGAAAGAGCAGAAGACAGTGGCAATGA-3'

(SEQ ID NO: 18)
HIVGao2R: 5'-AGCCCTTCCAGTCCCCCCTTTTCTTTTA-3'
```

Each well of a new PE2400 base received a 98 ul aliquot, followed by 2 ul of each primary PCR reaction serving as a as template for the nested PCR reaction. The same cycle parameters as indicated for the primary PCR were applied.

Figure 4:
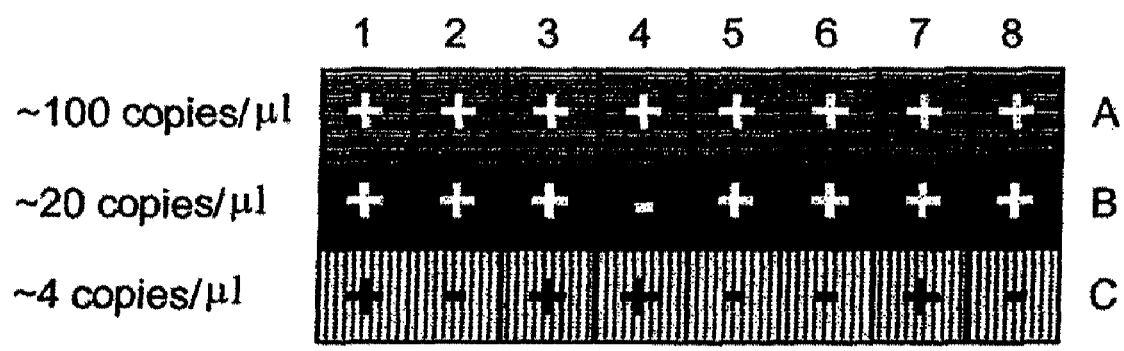

5. Gel analysis of RT-PCR products:
   a) 10 ul of each nested PCR product was run on a 1.5% agarose gel.
   b) Only the wells of the original RNA template dilution that produced approximately 50% positive wells were cloned/sequenced to ensure cloning/sequencing of an amplicion derived from a single RNA template molecule. For example, if gel analysis produced the following pattern based on the original RT layout, only the 4 positive wells of the last row (the 1:25 or ~4 copies/ul row) would be cloned/sequenced (FIG. 4). All other positives were discarded.
   c) The chosen positives were either cloned or sent directly for sequencing.

6. Cloning of RT-PCR products:
   a) PCR reaction products were purified using Qiagen's Gel Extraction Kit according to the manufacturer's standard protocol.
   b) Amplicons were cloned into Promega's pTarget Mammalian Expression vector following a standard protocol, such as that which is included with the pTarget Kit. Each selected positive reaction was cloned once. In addition, only one clone from each plate was picked/analyzed to ensure that the minority species were fully represented
   c) Plasmid DNA was prepared according to standard procedures for ABI sequencing.

7. ABI sequencing of RT-PCR products or clones:
   a) Standard automated sequencing on an ABI 370 series sequencing machine was carried out. The following three primers were used to ensure complete redundant sequencing of the V3 loop of the envelope gene:

NL6942F: 5'-GCACAGTACAATGTACACATG-3' (SEQ ID NO: 19)

NL7103F: 5'-ACAAGACCCAACAACAATACA-3' (SEQ ID NO: 20)

NL7356R: 5'-TGTATTGTTGTTGGGTCTTGT-3' (SEQ ID NO: 21)

8. Sequence analysis:
 a) The DNA sequence of the env V3 loop was determined.
 b) Protein translation of the V3 loop was determined.
 c) CCR5 or CXCR4 predictions were based on the scheme outlined below:

```
                   268                                      290
Clade B             |                                        |
consensus: N N T R K - I - I G P G - A - - - T G - I I G  (SEQ ID NO: 35)
```

R5 strain if 1. G/S at residue 273 and D/E at residue 287 (SEQ ID NO: 22)
2. K,H,R at residue 275 and D/E at residue 287 (SEQ ID NO: 23)
3. Not K,H,R at residue 275 but D/E/K/H/R at residue 287 (SEQ ID NO: 24)

X4 strain if: 1. K,H,R at residue 275 and K/H/R at residue 287 (SEQ ID NO: 25)

d) The lambda value for the patient was calculated as:

$\lambda = (\# \text{ of } R5 \text{ clones})/(\text{total \# of clones})$

Having thus described in detail preferred embodiments of the present invention, it is to be understood that the invention defined by the appended claims is not to be limited to particular details set forth in the above description as many apparent variations thereof are possible without departing from the spirit or scope of the present invention.

---

The invention claimed is:

1. A diagnostic method of monitoring therapeutic efficacy of an antiretroviral therapy in an acquired immunodeficiency virus-infected patient undergoing the antiretroviral therapy, comprising:
   (a) obtaining from the virus-infected patient a population of acquired immunodeficiency virus;
   (b) determining the proportion of the viral population using a CXCR4 coreceptor; and
   (c) determining the proportion of the viral population using a CCR5 coreceptor,
   wherein the proportion of the viral population using the CXCR4 coreceptor and the proportion of the viral population using the CCR5 coreceptor, is determined by obtaining virus envelope gene V3 region sequence(s), whereby the antiretroviral therapy is determined to be therapeutically effective when the proportion of the viral population using the CXCR4 coreceptor is lower than the proportion of the viral population using the CCR5 coreceptor.

2. The diagnostic method according to claim 1, wherein the envelope gene encodes gp160 or gp120.

3. The diagnostic method according to claim 1, wherein the acquired immunodeficiency virus is HIV-1 or HIV-2.

4. The diagnostic method according to claim 1, wherein the sequence of the envelope gene V3 region is determined from a DNA micro-chip array.

5. The diagnostic method according to claim 1, wherein the antiretroviral therapy is highly active antiretroviral therapy (HAART), protease inhibitors, fusion inhibitors, integrase inhibitors, coreceptor specific agents, 3TC, AZT, nevirapine, non-nucleoside analogue reverse transcriptase inhibitors, or nucleoside analogue reverse transcriptase inhibitors.

6. The diagnostic method according to claim 1, wherein the antiretroviral therapy is a combination therapy.

7. The diagnostic method according to claim 6, wherein the combination therapy comprises one or more antiretroviral therapies selected from highly active antiretroviral therapy (HAART), protease inhibitors, fusion inhibitors, integrase inhibitors, coreceptor specific agents, 3TC, AZT, nevirapine, non-nucleoside analogue reverse transcriptase inhibitors, and nucleoside analogue reverse transcriptase inhibitors.

* * * * *

UNITED STATES PATENT AND TRADEMARK OFFICE
CERTIFICATE OF CORRECTION

| | | |
|---|---|---|
| PATENT NO. | : 7,943,297 B2 | Page 1 of 1 |
| APPLICATION NO. | : 11/872842 | |
| DATED | : May 17, 2011 | |
| INVENTOR(S) | : Sean Philpott et al. | |

It is certified that error appears in the above-identified patent and that said Letters Patent is hereby corrected as shown below:

Column 1, line 17, please replace the following paragraph:

"STATEMENT OF RIGHTS TO INVENTIONS MADE UNDER FEDERALLY SPONSORED RESEARCH

This work was supported by the government, in part, by Grant U01A135004 from the National Institute for Allergy and Infectious Diseases and a National Research Service Award (1F32HD08478-01) from the National Institute of Child Health and Human Development. The government may have certain rights to this invention."

with

--STATEMENT REGARDING FEDERALLY SPONSORED RESEARCH OR DEVELOPMENT

This invention was made with government support under AI0135004 & HD008478 awarded by the National Institutes of Health. The government has certain rights in the invention.--

Signed and Sealed this
Nineteenth Day of February, 2013

Teresa Stanek Rea
*Acting Director of the United States Patent and Trademark Office*